United States Patent [19]
Travis et al.

[11] Patent Number: 5,523,390
[45] Date of Patent: Jun. 4, 1996

[54] PORPHYROMONAS GINGIVALIS ARGININE-SPECIFIC PROTEINASE

[75] Inventors: James Travis; Jan S. Potempa, both of Athens,, Ga.; Philip J. Barr, Berkeley; Nadine Pavloff, Novato, both of Calif.

[73] Assignee: University of Georgia Research Foundation, Inc., Athens, Ga.

[21] Appl. No.: 119,361

[22] Filed: Sep. 10, 1993

[51] Int. Cl.$^6$ .............................. C12N 9/14; C12N 9/48; C12N 9/52; C07H 19/00
[52] U.S. Cl. ...................... 536/23.2; 435/195; 435/212; 435/213; 435/220; 435/69.1; 435/320.1; 536/22.1; 536/23.1; 536/23.7
[58] Field of Search ...................................... 435/195, 212, 435/213, 220, 320.1, 69.1; 536/22.1, 23.1, 23.2, 23.7

[56] References Cited

PUBLICATIONS

Lee et al. "Generation of cDNA Probes Directed by Amino Acid . . . " *Science* vol. 239, 1288–1291 Mar. 11, 1988.
Otogoto et al. (1993) "Isolation and Characterization of the *Porphyromonas gingivalis* prT Gene, Coding for Protease Activity", *Infect. & Immun.* 1(61):117–123.
Park et al. (1992) "Cloning of a *Porphyromonas (Bacteroides) gingivalis* Protease Gene and Characterization of its Product", *FEMS Microb. Lett.* 92:273–278.
Shah et al. (1992) "Evidence for Independent Molecular Identity and Functional Interaction of the Haemagglutinin and Cysteine Proteinase (gingivain) of *Porphyromonas gingivalis*", *J. Med. Microbiol.* 36:239–244.
Nishikata et al. (1991) "Characterization of *Porphyromonas (Bacteroides) gingivalis* Hemagglutinin as as Protease", *Biochem. & Biophys. Res. Comm.* 1(178):336–342.
Roberts et al. (1990) "Purification of the Secreted Thiol–activated Protease of *Porphyromonas (Bacteroides) gingivalis* and the Cloning and Expression of the Gene in *Escherichia coli*", *Clinical & Molecular Aspects of Anaerobes* (ed.) S. P. Borriello, pp. 227–233.
Chen et al. (1992) "Purification and Characterization of a 50–kDa Cysteine Proteinase (Gingipain) from *Porphyromonas gingivalis*," *J. Biol. Chem.* 267:18896–18901.
Wingrove et al. ((1992) "Activation of Complement Components C3 and C5 by a Cysteine Proteinase (Gingipain–1) from *Porphyromonas (Bacteroids) gingivalis*," *J. Biol. Chem.* 287: 18902–18907.
Chen et al. (1991) "Stimulation of Proteinase and Amidase Activities in *Porphyromonas (Bacteroides) gingivalis* by Amino Acids and Dipeptides," *Infect. Immun.* 59: 2846–2850.
Travis et al. (1991) "Bacterial Proteinases in Periodontal Disease," Abstract, *J. Cell Biochem.* Suppl. O (15 Part G), 117.
Potempa et al. (1991) "Purification and Characterization of a 50 kD Cysteine Proteinase of *Porphyromonas gingivalis*," Abstract, *FASEB J.* 5(4) A829.

Hugli et al. (1991) "A Role for Complement in Gingivitis: Acitivation by a Cysteine Protease from *Porphyromonas gingivalis*," Abstract, *Clin. Exp. Immunol.* 86(Suppl. 1), 20.
Schenkein, H. A. (1988) "The Effect of Periodontal Proteolytic Bacteroides Species on Proteins of the Human Complement System," *J. Periodontal Res.* 23: 187–192.
Tsutsui et al. (1987) "Purification and Characterization of a Protease from *Bacteroides gingivalis* 381," *Infect. Immun.* 55: 420–427.
Yoshimura et al. (1984) "Characterization of a Trypsin–Like Protease from the Bacterium *Bacteroides gingivalis* Isolated from Human Dental Plaque," *Archs Oral Biol.* 29: 559–564.
Suido et al. (1987) "Characterization of N–CBz–glycyl–glycyl–arginyl peptidase and glycyl–prolyl peptidase of *Bacteroides gingivalis*," *J. Periodont, Res.* 22: 412–418.
Birkedal–Hansen et al. (1988) "Characterization of Collagenolytic Activity from Strains of *Bacteroides gingivalis*," *J. Periodontal Res.* 23: 258–264.
Grenier et al. (1989) "Characterization of Sodium Dodecyl Sulfate–Stable *Bacteroides gingivalis* Proteases by Polyacrylamide Gel Electrophoresis," *Infect. Immun.* 57: 95–99.

(List continued on next page.)

*Primary Examiner*—Robert A. Wax
*Assistant Examiner*—Hyosuk Kim
*Attorney, Agent, or Firm*—Greenlee and Winner

[57] ABSTRACT

Provide herein is a substantially pure gingipain-1 preparation, gingipain-1 being characterized as having an apparent molecular mass of 50 kDa as estimated by sodium dodecyl sulfate polyacrylamide gel electrophoresis and an apparent molecular mass of 44 kDa as estimated by gel filtration chromatography, said gingipain-1 having amidolytic and proteolytic activity for cleavage after arginine residues and having no amidolytic and/or proteolytic activity for cleavage after lysine residues, wherein the amidolytic and/or proteolytic activity is inhibited by cysteine protease group-specific inhibitors including iodoacetamide, iodoacetic acid, N-ethylmaleimide, leupeptin, antipain, trans-epoxysuccinyl-L-leucylamido-(4-guanidino)butane, TLCK, TPCK, p-aminobenzamidine, N-chlorosuccinamide, and chelating agents including EDTA and EGTA, wherein the amidolytic and/or proteolytic activity of said gingipain-1 is not sensitive to inhibition by human cystatin C, α2-macroglobulin, α1-proteinase inhibitor, antithrombin III, α2-antiplasmin, serine protease group-specific inhibitors including diisopropylfluorophosphate, phenylmethyl sulfonylfluoride and 3,4-diisochlorocoumarin, and wherein the amidolytic and/or proteolytic activities of gingipain-1 are stabilized by $Ca^{2+}$ and wherein the amidolytic and/or proteolytic activities of said gingipain-1 are stimulated by glycine-containing peptides and glycine analogues, and methods for preparation. As specifically exemplified, Arg-gingipain-1 and Arg-gingipain-2 are purified from *Porphyromonas gingivalis*, and the mature Arg-gingipain-2 has an amino acid sequence as given in SEQ ID NO:5 from amino acid 1 through amino acid 510. Also provided are nucleic acid sequences encoding Arg-gingipain-2. The nucleotide coding sequence of the mature Arg-gingipain-2 is given in SEQ ID NO:4, from nucleotide 1630 through nucleotide 3105.

2 Claims, 6 Drawing Sheets

PUBLICATIONS

Uitto V. J. (1987) "Human Gingival Proteases. 1: Extraction and Preliminary Characterization of Trypsin–like and Elastase–like Enzymes"; J. Periodontal Res. 22:58–63.

Ono et al. (1987) "Purification and Characterization of a Thiol–protease from *Bacteroides gingivalis* Strain 381"; Oral Micro. Immun. 2:77–81.

Sorsa et al. (1987) "A Trypsin–like Protease from *Bacteroides gingivalis:* Partial Purification and Characterization"; J. Periodont Res. 22:375–380.

Otsuka et al. (1987) "Isolation and Characterization of Protease from Culture Supernatant of *Bacteroides gingivalis*"; J. Periodont Res. 22:491–498.

Fujimura et al. (1986) "Isolation and Characterization of a Protease from *Bacteroides gingivalis*" Infect. Immun. 3(vol. 55):716–720.

- In the absence of Gly-Gly
○ In the presence of 50mM-Gly-Gly

PORPHYROMONAS GINGIVALIS ARGININE-SPECIFIC PROTEINASE

This invention was made, at least in part, with funding from the National Institutes of Health (Grant Nos. DE 09761, HL 26148 and HL 37090). Accordingly, the United States Government may have certain rights in this invention.

FIELD OF THE INVENTION

The field of this invention is bacterial proteases, more particularly those of *Porphyromonas gingivalis*, most particularly the arginine-specific protease termed gingipain-1 herein.

BACKGROUND OF THE INVENTION

*Porphyromonas gingivalis* (formerly *Bacteroides gingivalis*) is an obligately anaerobic bacterium which is implicated in periodontal disease. *P. gingivalis* produces proteolytic enzymes in relatively large quantities; these proteinases are recognized as important virulence factors [Smalley et al. (1989) *Oral Microbiol. Immun.* 4, 178–179; Marsh et al. (1989) *FEMS Microbiol, Lett.* 59, 181–186; Grenier and Mayrand (1987) *J. Clin. Microbiol*, 25, 738–740]. A number of physiologically significant proteins, including collagen [Birkedal-Hansen et al. (1988) *J. Periodontal Res.* 23, 258–264; Sundqvist et al. (1987) *J. Periodontal Res.* 22, 300–306]; fibronectin [Wikstrom and Linde (1986) *Infect. Immun.* 51, 707–711; Uitto et al. (1989) *Infect. Immun.* 57, 213–218]; immunoglobulins [Kilian, M. (1981) *Infect. Immun.* 34, 757–765; Sundqvist et al. (1985) *J. Med. Microbiol*, 19, 85–94; Sato et al. (1987) *Arch. Oral Biol.* 32, 235–238]; complement factors C3, C4, C5, and B [Sundqvist, et al. 1985) supra; Schenkein, H. A. (1988) *J. Periodontal Res.* 23, 187–192]; lysozyme [Otsuka et al. (1987) *J. Periodontal Res.* 22, 491–498]; iron-binding proteins [Carlsson et al. (1984) *J. Med. Microbiol*, 18, 39–46]; plasma proteinase inhibitors [Carlsson et al. (1984) *Infect. Immun.* 43, 644–648; Herrmann et al. (1985) *Scand. J. Dent. Res.* 93, 153–157]; fibrin and fibrinogen [Wikstrom et al. (1983) *J. Clin. Microbiol.* 17, 759–767; Lantz et al. (1986) *Infect. Immun.* 54, 654–658]; and key factors of the plasma coagulation cascade system [Nilsson et al. (1985) *Infect. Immun.* 50, 467–471], are hydrolyzed by proteinases from this microorganism. Such broad proteolytic activity may play a major role in the evasion of host defense mechanisms and the destruction of gingival connective tissue associated with progressive periodontitis [Saglie et al. (1988) *J. Periodontol.* 59, 259–265].

Progressive periodontitis is characterized by acute tissue degradation promoted by collagen digestion and a vigorous inflammatory response characterized by excessive neutrophil infiltration [White and Maynard (1981) *J. Periodontal Res.* 16, 259–265]. Gingival crevicular fluid accumulates in periodontitis as gingival tissue erosion progresses at the foci of the infection, and numerous plasma proteins are exposed to proteinases expressed by the bacteria at the injury site. It was speculated that neutrophils may have been recruited to the gingiva, in part, by the humoral chemotactic factor C5a. The complement components C3 and C5 are activated by complex plasma proteases with "trypsin-like" specificities called convertases [Muller-Eberhard (1988) *Ann. Rev. Biochem.* 57, 321–347]. The human plasma convertases cleave the α-chains of C3 and C5 at a specific site generating biologically active factors known as anaphylatoxins (i.e. C3a and C5a). The anaphylatoxins are potent proinflammatory factors exhibiting chemotactic and/or spasmogenic activities as well as promoting increased vascular permeability. The larger products from C3 and C5 cleavage (i.e. C3b and C5b) participate in functions including complement cascade activation, opsinization, and lytic complex formation.

There are conflicting data as to the number and types of proteinases produced by *P. gingivalis*. In the past, proteolytic activities of *P. gingivalis* were classified into two groups; those enzymes which specifically degraded collagen and the general "trypsin-like" proteinases which appeared to be responsible for other proteolytic activity. Trypsin (and trypsin-like proteases) cleaves after arginine or lysine in the substrates [See, e.g. Lehninger A. L. (1982), *Principles of Biochemistry*, Worth Publishing, Inc., New York]. The Arg-gingipain described herein differ in that they are specific for cleavage after only arginine, with no activity for cleavage after lysine residues.

More recently, Birkedal-Hansen et al. [Birkedal-Hansen, et al. (1988) supra.] performed a systematic analysis of the effect of six classes of proteinase inhibitors on Porphyromonas collagenolytic activity which strongly suggested that all proteinases from this organism are dependent on free cysteine groups and metal ions, as indicated by inhibition by thiol-blocking reagents and metal chelators. On the other hand, Grenier et al. [Grenier et al. (1989) *Infect Immun.* 57, 95–99] identified at least eight proteolytic enzymes with molecular masses in the range of 29–110 kDa. Two of these appeared to be serine proteinases with glycyl-prolyl peptidase activity, one of which appears to be about 29 kDa [Grenier and McBride (1987) *Infect. Immun.* 55, 3131–3136].

All other enzymes were shown to be activated by cysteine and hydrolyzed the synthetic substrate Benzoyl-L-Arginyl-p-Nitroanilide (Bz-L-Arg-p-NA). Whether this represent distinct proteolytic enzymes or autocatalytic products of a single proteinase remains to be established. Although many attempts have been made to separate one of these trypsin-like proteinases [Otsuka, et al. (1987) supra.; Ono et al. (1987) *Oral Microbiol. Immunol.* 2, 77–81; Fujimura and Nakamura (1987) *Infect. Immun.* 55, 716–720; Suido et al. (1987) *J. Periodontal Res.* 22, 412–418; Tsutsui et al. (1987) *Infect. Immun.* 55, 420–427; Uitto, V. J. (1987) *J. Periodontal Res.* 22, 58–63; Sorsa et al. (1987) *J. Periodontal Res.* 22, 375–380] until now none has been purified sufficiently for rigorous biochemical and enzymological characterization. In this application, a 50 kDa trypsin-like, thiol-activated proteinase of *P. gingivalis*, which has been purified to apparent homogeneity for the first time, is described and termed gingipain-1 herein.

There is a need in the art for purified Arg-gingipain, for example, as antigen for preparing antibodies specific to this protein or for vaccines useful in protection against periodontal disease, and for studies to identify inhibitors of this enzyme.

SUMMARY OF THE INVENTION

An object of the present invention is to provide a proteinase preparation comprising a substantially pure low molecular weight Arg-gingipain, termed Arg-gingipain-1 (or gingipain-1), herein, said gingipain-1 having an apparent molecular mass of 50 kDa as estimated by sodium dodecyl sulfate polyacrylamide gel electrophoresis and an apparent molecular mass of 44 kDa as estimated by gel filtration chromatography, said gingipain-1 having amidolytic and proteolytic activity for cleavage after arginine residues and having no amidolytic and/or proteolytic activity for cleavage after lysine residues, wherein the amidolytic and/or proteolytic activity is inhibited by cysteine protease group-specific inhibitors including iodoacetamide, iodoacetic acid, N-ethylmaleimide, leupeptin, antipain,trans-epoxysuccinyl-L-leucylamido-(4-guanidine)butane, TLCK, TPCK, p-aminobenzamidine, N-chlorosuccinamide, and chelating agents including EDTA and EGTA, wherein the amidolytic and/or proteolytic activity of said gingipain-1 is not sensitive to inhibition by human cystatin C, α2-macroglobulin, α1-proteinase inhibitor, antithrombin III, α2-antiplasmin, serine protease group-specific inhibitors including diisopropylfluorophosphate, phenylmethyl sulfonylfluoride and 3,4-diisochlorocoumarin, and wherein the amidolytic and/or proteolytic activities of gingipain-1 are stabilized by $Ca^{2+}$ and wherein the amidolytic and/or proteolytic activities of said gingipain-1 are stimulated by glycine-containing peptides and glycine analogues. In a specifically exemplified gingipain-1 protein, the protein is characterized by an N-terminal amino acid sequence as given in SEQ ID NO:1 Tyr-Thr-Pro-Val-Glu-Glu-Lys-Gln-Asn-Gly-Arg-Met-Ile-Val-Ile-Val-Ala-Lys-Lys-Tyr-Glu-Gly-Asp-Ile-Lys-Asp-Phe -Val-Asp-Trp-Lys-Asn-Gln-Arg-Gly-Leu-Thr-Lys-Xaa-Val-Lys-Xaa-Ala and by a C-terminal amino acid sequence as given in SEQ ID NO:6 (Glu-Leu-Leu-Arg).

A further object of this invention is a high molecule weight form of Arg-gingipain, termed Arg-gingipain-2 herein, and prepared as described in Example 1.7.

As specifically exemplified, a mature gingipain-2 protein has a complete deduced amino acid sequence as given in SEQ ID NO:5 from amino acid 1 through amino acid 510.

It is an additional object of the invention to provide a method for the preparation of a substantially pure Arg-gingipain-1 protein. Said substantially pure Arg-gingipain-1 exhibits amidolytic and/or proteolytic activity with specificity for cleavage after arginine, but exhibits no amidolytic and/or proteolytic activity with specificity for cleavage after lysine residues. The purification method exemplified herein comprises the steps of precipitating extracellular protein from cell-free culture supernatant of *Porphyromonas gingivalis* with ammonium sulfate (90% w/v saturation), fractionating the precipitated proteins by gel filtration, further fractionating by anion exchange chromatography those proteins in the fractions from gel filtration with the highest specific activity for amidolytic activity as measured with Benzoyl-L-arginyl-p-nitroanilide and collecting those proteins which were not bound to the anion exchange column, and fractionating those proteins by FPLC over a cation exchange column (MonoS HR5/5, Pharmacia, Piscataway, N.J.) and finally separating gingipain-1 from lysine-specific proteolytic/amidolytic protein(s) by affinity chromatography over L-arginyl-agarose. Preferably the *P. gingivalis* used is strain H66, and preferably the culture is grown to early stationary phase. Arg-gingipain-1 can also be purified from cells using appropriate modifications of the foregoing procedures (cells must be disrupted, e.g., by lysis in a French pressure cell). Preferably the gel filtration step is carried out using Sephadex G-150, the anion exchange chromatography step is carried out using diethylaminoethyl (DEAE)-cellulose, the FPLC step is carried out using Mono S, and the affinity chromatography is carried out using L-arginyl-Sepharose 4B.

It is a further object of this invention to provide recombinant polynucleotides (e.g., a recombinant DNA molecule) comprising a nucleotide sequence encoding an Arg-gingipain protein, preferably having an amino acid sequence as given in SEQ ID NO:5 from amino acid 1 through amino acid 510. As specifically exemplified herein, the nucleotide sequence encoding a mature Arg-gingipain protein is given in SEQ ID NO:4 from nucleotides 1630 through 3105. The skilled artisan will understand that the amino acid sequence of the exemplified gingipain protein can be used to identify and isolate additional, nonexemplified nucleotide sequences which will encode a functional protein of the same amino acid sequence as given in SEQ ID NO:5 from amino acid 1 through amino acid 510 or an amino acid sequence of greater than 90% identity and having equivalent biological activity. The skilled artisan understands that it may be desirable to express the Arg-gingipain as a secreted protein; if so, he knows how to modify the exemplified coding sequence for the "mature" gingipain-2 by adding a nucleotide sequence encoding a signal peptide appropriate to the host in which the sequence is expressed. When it is desired that the sequence encoding an Arg-gingipain protein be expressed, then the skilled artisan will operably link transcription and translational control regulatory sequences to the coding sequences, with the choice of the regulatory sequences being determined by the host in which the coding sequence is to be expressed. With respect to a recombinant DNA molecule carrying an Arg-gingipain coding sequence, the skilled artisan will choose a vector (such as a plasmid or a viral vector) which can be introduced into and which can replicate in the host cell. The host cell can be a bacterium, preferably *Escherichia coli*, or a yeast or mammalian cell.

In another embodiment, recombinant polynucleotides which encode an Arg-gingipain, including, e.g., protein fusions or deletions, as well as expression systems are provided. Expression systems are defined as polynucleotides which, when transformed into an appropriate host cell, can express a proteinase. The recombinant polynucleotides possess a nucleotide sequence which is substantially similar to a natural Arg-gingipain-encoding polynucleotide or a fragment thereof.

The polynucleotides include RNA, cDNA, genomic DNA, synthetic forms, and mixed polymers, both sense and antisense strands, and may be chemically or biochemically modified or contain non-natural or derivatized nucleotide bases. DNA is preferred. Recombinant polynucleotides comprising sequences otherwise not naturally occurring are also provided by this invention, as are alterations of a wild type proteinase sequence, including but not limited to deletion, insertion, substitution of one or more nucleotides or by fusion to other polynucleotide sequences.

The present invention also provides for fusion polypeptides comprising an Arg-gingipain. Homologous polypeptides may be fusions between two or more proteinase sequences or between the sequences of a proteinase and a related protein. Likewise, heterologous fusions may be constructed which would exhibit a combination of properties or activities of the proteins from which they are derived. Fusion partners include but are not limited to immunoglobulins, ubiquitin bacterial β-galactosidase, trpE, protein A, β-lactamase, alpha amylase, alcohol dehydrogenase and yeast alpha mating factor, [Godowski et al. (1988) *Science*, 241, 812–816]. Fusion proteins will typically be made by recombinant methods but may be chemically synthesized.

Compositions and vaccine preparations comprising substantially purified Arg-gingipain derived from *P. gingivalis* and a suitable carrier therefor are provided. Such vaccines are useful, for example, in immunizing an animal, including humans, against inflammatory response and tissue damage caused by *P. gingivalis* in periodontal disease. The vaccine preparations comprise an immunogenic amount of a proteinase or an immunogenic fragment or subunit thereof. Such vaccines may comprise one or more Arg-gingipain proteinases, or an Arg-gingipain in combination with another protein or other immunogen. By "immunogenic amount" is meant an amount capable of eliciting the production of antibodies directed against one or more Arg-gingipains in an individual to which the vaccine has been administered.

BRIEF DESCRIPTION OF THE FIGURES

FIG. 6 is the model proposed for the cleavage of human C5 by Arg-gingipain-1. The two chains of C5 are represented by bars, and the hexagons labeled CHO represent the attachment sites of the N-linked oligosaccharides. The arrows labeled 1° and 2° denote the primary and secondary sites for cleavage by gingipain-1. The secondary site between residues 74 and 75 is not the only site for cleavage as degradation progresses, but is identified as a known site, based on the release of biologically active C5a.

DETAILED DESCRIPTION OF THE INVENTION

Figure 1:
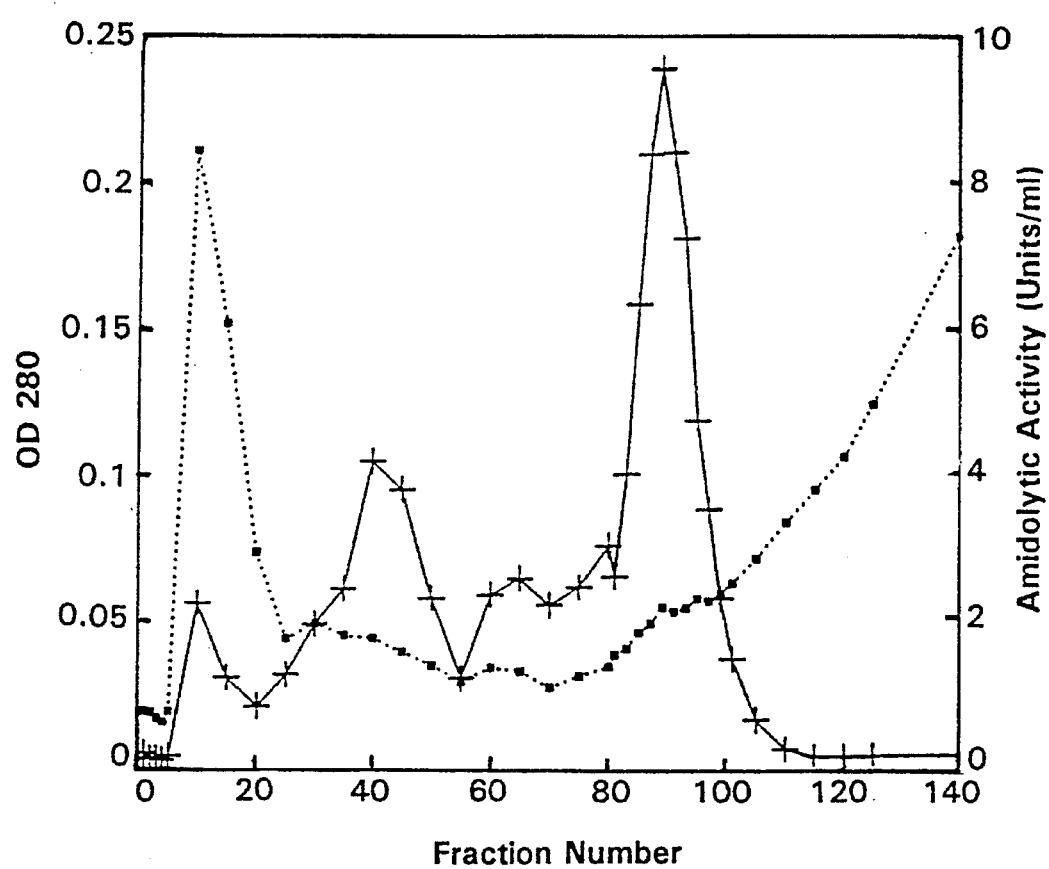
FIG. 1 illustrates the results of gel exclusion chromatography of the 90% $(NH_4)_2SO_4$ precipitated protein fraction (from *P. gingivalis* culture supernatant). Protein content was tracked by monitoring $A_{280}$ (. . . ■ . . .) and amidolytic activity was measured using Bz-L-Arg-pNA as substrate (-+-).

Abbreviations used herein for amino acids are standard in the art: X or Xaa represents an amino acid residue that has not yet been identified but may be any amino acid residue including but not limited to phosphorylated tyrosine, threonine or serine, as well as cysteine or a glycosylated amino acid residue. The abbreviations for amino acid residues as used herein are as follows: A, Ala, alanine; V, Val, valine; L, Leu, leucine; I, Ile, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine. Other abbreviations used herein include Bz, benzoyl; Cbz, carboxybenzoyl; pNA, p-nitroanilide; MeO, methoxy; Suc, succinyl; OR, ornithyl; Pip, pipecolyl; SDS, sodium dodecyl sulfate; TLCK, tosyl-L-lysine chloromethyl ketone; TPCK, tosyl-L-phenylalanine chloromethyl ketone; S-2238, D-Phe-Pip-Arg-pNA, S-2222, Bz-Ile-Glu-($\gamma$-OR)-Gly-pNA; S-2288, D-Ile-Pro-Arg-pNA; S-2251, D-Val-Leu-Lys-pNA; Bis-Tris, 2-[bis(2-hydroxyethyl)amino]-2-(hydroxymethyl)-propane-1,3-diol; FPLC, fast protein liquid chromatagraphy; HPLC, high performance liquid chromatography; Tricine, N-[2-hydroxy-1,1-bis(hydroxymethyl)ethyl]glycine; EGTA, [ethylene-bis(oxyethylene-nitrile)tetraacetic acid; EDTA, ethylenediamine-tetraacetic acid; Z-L-Lys-pNa, Z-L-Lysine-p-Nitroanilide.

Arg-gingipain is the term given to a *P. gingivalis* enzyme with specificity for proteolytic and/or amidolytic activity for cleavage of an amide bond, in which L-arginine contributes the carboxyl group. The Arg-gingipains described herein have identifying characteristics of cysteine dependence, inhibition response as described, $Ca^{2+}$-stabilization and glycine stimulation. Particular forms of Arg-gingipain are distinguished by their apparent molecular masses of the mature proteins (as measured without boiling before SDS-PAGE). Arg-gingipains of the present invention have no amidolytic or proteolytic activity for amide bonds in which L-lysine contributes the —COOH moiety.

Arg-gingipain is the name given herein to a protein characterized as having a molecular mass of 50 kDa as measured by SDS-PAGE and 44 kDa as measured by gel filtration over Sephadex G-150, having amidolytic and/or proteolytic activity for substrates having L-Arg in the $P_1$ position, i.e. on the N-terminal side of the peptide bond to be hydrolyzed but having no activity against corresponding lysine-containing substrates being dependent on cysteine (or other thiol groups for full activity), having sensitivity to cysteine protease group-specific inhibitors including iodoacetamide, iodoacetic acid, and N-methylmaleimide, leupeptin, antipain, trans-epoxysuccinyl-L-leucylamido-(4-guanidino)butane, TLCK, TPCK, p-aminobenzamidine, N-chlorosuccinamide, and chelating agents including EDTA and EGTA, but being resistant to inhibition by human cystatin C, α2-macroglobulin, α1-proteinase inhibitor, antithrombin III, α2-antiplasmin, serine protease group-specific inhibitors including diisopropylfluorophosphate, phenylmethyl sulfonylfluoride and 3,4-diisochlorocoumarin, and wherein the amidolytic and/or proteolytic activities of gingipain-1 are stabilized by $Ca^{2+}$ and wherein the amidolytic and/or proteolytic activities of said gingipain-1 are stimulated by glycine-containing peptides and glycine analogues.

An exemplified Arg-gingipain described herein exists in the native form in a high molecular weight form, having an apparent molecular mass of 95 kDa as determined by SDS-PAGE, without boiling of samples. When boiled, the high molecular weight form appears to dissociate into components of 50 kDa, 43 kDa, 27 kDa and 17 kDa. Arg-gingipain-2 is the name given to the 50 kDa, enzymatically active component of the high molecular weight complex.

The complete amino acid sequence of an exemplified mature Arg-gingipain is given in SEQ ID NO:5, from amino acid 1 through amino acid 510. In nature this protein is produced by the archebacterium *Porphyromonas gingivalis*; it can be purified from cells or from culture supernatant using the methods provided herein. Without wishing to be bound by any theory, it is proposed that this sequence corresponds to Arg-gingipain-2.

As used herein with respect to Arg-gingipain-1, a substantially pure Arg-gingipain preparation means that there is only one protein band visible after silver-staining an SDS polyacrylamide gel run with the preparation, and the only amidolytic and/or proteolytic activities are those with specificity for L-arginine in the $P_1$ position relative to the bond cleaved. A substantially pure high molecular weight Arg-gingipain preparation has only one band (95 kDa) on SDS-PAGE (sample not boiled) or four bands (50 kDa, 43 kDa, 27 kDa, 17 kDa; sample boiled). No amidolytic or proteolytic activity for substrates with lysine in the $P_1$ position is evident in a substantially pure high molecular weight or Arg-gingipain-2 preparation. Furthermore, a substantially pure preparation of Arg-gingipain has been separated from components with which it occurs in nature. Substantially pure Arg-gingipain is substantially free of naturally associated components when separated from the native contaminants which accompany them in their natural state. Thus, Arg-gingipain that is chemically synthesized or synthesized in a cellular system different from the cell from which it naturally originates will be substantially free from its naturally associated components. Techniques for synthesis of polypeptides are described, for example, in Merrifield (1963) *J. Amer. Chem. Soc.*, 85, 2149–2156.

A chemically synthesized Arg-gingipain protein is considered an "isolated" polypeptide, as is an Arg-gingipain produced as an expression product of an isolated proteinase-encoding polynucleotide which is part of an expression vector (i.e., a "recombinant proteinase"), even if expressed in a homologous cell type.

Recombinant Arg-gingipain-1 or Arg-gingipain-2 can be obtained by culturing host cells transformed with the recombinant polynucleotides comprising nucleotide sequences encoding an Arg-gingipain as described herein under conditions suitable to attain expression of the proteinase-encoding sequence.

Example 1 below describes the purification of Arg-gingipain-1 and Arg-gingipain-2 from *P. gingivalis* culture supernatant, i.e., from a natural source. Various methods for the isolation of an Arg-gingipain from other biological material, such as from nonexemplified strains of *P. gingivalis* or from cells transformed with recombinant polynucleotides encoding such proteins, may be accomplished by methods known in the art. Various methods of protein purification are known in the art, including those described, e.g., in *Guide to Protein Purification*, ed. Deutscher, Vol. 182 of *Methods in Enzymology* (Academic Press, Inc.: San Diego, 1990) and Scopes, *Protein Purification: Principles and Practice* (Springer-Verlag: New York, 1982).

The purification of Arg-gingipain-1 has been described in Chen et al. (1992) *J. Biol. Chem.* 267, 18896–18901. One major problem overcome in the purification of the arginine-specific proteinase of *P. gingivalis* involved the removal of the large quantity of hemin and protohemin found to be present in the spent medium after growth of this bacterium. This was accomplished, in part, by gel filtration after ammonium sulfate precipitation of cell-free proteins (90% ammonium sulfate saturation). Chromatography over Sephadex G-150 yielded four peaks with Bz-L-Arg-pNA-hydrolyzing activity (see FIG. 1). In each of these fractions, the hydrolytic activity was dependent on cysteine and enhanced many-fold by the addition of glycyl-glycine or glycine amide. Peak 4 was further studied because it exhibited the highest specific activity. However, it has been determined the antibody specific for gingipain-1 immunoprecipitates proteinase from all four Sephadex G-150 peaks.

Without wishing to be bound by any particular theory, it is postulated that the four-peak Bz-L-Arg-pNA-amidolytic profile is an anomaly resulting from the binding of gingipain-1 to membrane or nucleic acid fragments. Alternatively, those peaks containing higher molecular weight protein may contain partially processed gingipain-1 precursors. Although the purification of gingipain-1 as exemplified is from extracellular protein, it can also be purified from the bacterial cells.

Further analysis (see Example 1.7) of the high molecular weight fractions containing Arg-specific amidolytic and proteolytic activity revealed that Arg-gingipain-2 occurred non-covalently bound to proteins of 44 kDa, subsequently identified tentatively as hemagglutinin(s), and 27 kDa and 17 kDa. The N-terminal amino acid sequence of the complexed 44 kDa protein was Ser-Gly-Gln-Ala-Glu-Ile-Val-Leu-Glu-Ala-His-Asp-Val-Xaa-Asn-Asp-Gly-(SEQ ID NO:10).

Arg-Gingipain-1 was further purified from the Sephadex G-150 Peak 4 protein mixture by further steps of anion exchange chromatography over DEAE-cellulose and two runs over Mono S FPLC see (Table 1).

TABLE 1

Purification of *Porphyromonas gingivalis* gingipain-1

| Step | Protein $A_{280}$ | Activity[a] units | Specific Activity units/ $A_{280}$ | Purification fold | Yield % |
|---|---|---|---|---|---|
| Culture fluid | 26,400 | 7,428 | 0.3 | 1 | 100 |

TABLE 1-continued

Purification of *Porphyromonas gingivalis* gingipain-1

| Step | Protein $A_{280}$ | Activity[a] units | Specific Activity units/ $A_{280}$ | Purification fold | Yield % |
|---|---|---|---|---|---|
| $(NH_4)_2SO_4$ precipitate | 1,248 | 5,200 | 4.1 | 70 | 70 |
| Sephadex G-150 | 14 | 1,600 | 112 | 400 | 22 |
| DEAE-cellulose | 6 | 1,216 | 195 | 697 | 16 |
| Mono S FPLC | 2.5 | 852 | 342 | 1,223 | 11 |
| Mono S FPLC | 0.4 | 625 | 1,488 | 5,315 | 8 |

[a]Amidase activity using Bz-L-Arg-pNA; 1 unit = $A_{405nm}$ of 1.00/min/ml at 25° C.

As discussed in Example 1.2, Arg-gingipain-1 recovery was markedly reduced if an affinity chromatography step (L-Arginyl-Sepharose 4B) was used to remove trace amounts of a contaminating proteinase with specificity for cleavage after lysine residues.

Purified Arg-gingipain-1 exhibits an apparent molecular mass of about 50 KDa as determined by SDS-polyacrylamide gel electrophoresis. The size estimate obtained by gel filtration on Superose 12 (Pharmacia, Piscataway, N.J.) is 44 KDa. Amino-terminal sequence analysis through 43 residues gave a unique structure which showed no homology with any other proteins, based on a comparison in the protein NBRS data base, release 39.0. The sequence obtained is as follows:

Tyr-Thr-Pro-Val-Glu-Glu-Lys-Gln-Asn-Gly-Arg-Met-Ile-Val-Ile-Val-Ala-Lys-Lys-Tyr-Glu-Gly-Asp-Ile-Lys-Asp-Phe-Val-Asp-Trp-Lys-Asn-Gln-Arg -Gly-Leu-Thr-Lys-Xaa-Val-Lys-Xaa-Ala (SEQ ID NO:1). The C-terminal amino acid sequence of the gingipain-1 (major form recognized in zymography SDS-PAGE, 0.1% gelatin in gel), was found to be Glu-Leu-Leu-Arg. (SEQ ID NO:6). This corresponds to the amino acids encoded at nucleotides 3094–3105 in SEQ ID NO:4. This is consistent with the model for autoproteolytic processing of the precursor protein to produce the mature 50 kDa gingipain-1 protein.

Comparison of SEQ ID NO:1 with SEQ ID NO:5 shows differences at amino acids 37–38 of the mature Arg-gingipain. Without wishing to be bound by any theory, it is proposed that SEQ ID NO:4 comprises the coding sequence for Arg-gingipain-2, the enzymatically active component of the high molecular weight form of Arg-gingipain. This is consistent with the observation that there are at least two genes with substantial nucleic acid homology to the Arg-gingipain-specific probe.

Figure 2:
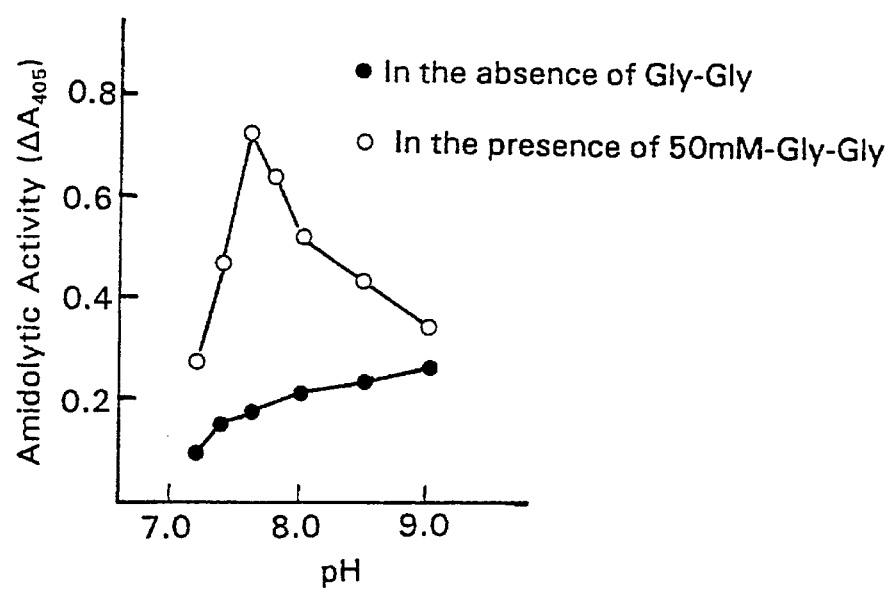
FIG. 2 illustrates the effect of assay pH on amidolytic activity of purified Arg-gingipain-1, as measured by $\Delta A_{405}$, in the presence (-O-) and absence (-●-) of 50 mM glycyl-glycine.

The enzymatic activity of Arg-gingipain-1 is stimulated by glycine and glycine-containing compounds. In the absence of a glycine-containing compound, the enzyme has essentially the same amidolytic activity in the pH range 7.5–9.0. However, in the presence of glycyl-glycine, e.g., substantial sharpening of the pH range for activity is observed, with the optimum being between pH 7.4 and 8.0 (FIG. 2). Preliminary kinetic data indicate that the effect of glycine and glycine analogues is to raise both $k_{cat}$ and $K_m$ equally so that the $k_{cat}/K_m$ ratio does not change. It is therefore likely that these compounds bind to the enzyme and/or substrate after an enzyme-substrate complex has already formed. The high molecular weight form is stimulated only about half as much by glycine compounds.

Arg-gingipain-1 requires cysteine for full amidolytic activity, and, although it is stimulated by other thiol-containing compounds (Table 2), the effect was less pronounced. Cysteine and cysteamine are most efficient, presumably because they perform the dual roles of reducing agents and glycine analogues.

TABLE 2

Effect of reducing agents on the amidolytic activity of gingipain-1

| Compound added mM | Activity –Gly—Gly % | +Gly—Gly[a] |
|---|---|---|
| None | 100 | 320 |
| Dithiothreitol | | |
| 0.1 | 159 | 636 |
| 1.0 | 432 | 1,814 |
| 10.0 | 685 | 1,905 |
| Mercaptoethanol | | |
| 0.1 | 165 | 627 |
| 1.0 | 456 | 1,860 |
| 10.0 | 685 | 2,010 |
| Glutathione | | |
| 0.1 | 208 | 853 |
| 1.0 | 593 | 2,550 |
| 10.0 | 770 | 3,100 |
| Cysteine | | |
| 0.1 | 685 | 2,740 |
| 1.0 | 1,212 | 4,985 |
| 10.0 | 1,844 | 5,290 |

[a]50 mM.

The amidolytic activity of Arg-gingipain-1 is inhibited by a number of —SH blocking group reagents oxidants, $Ca^{2+}$ chelating agents, and $Zn^{2+}$ (Table 3). The effect of the chelating agents EDTA and EGTA was reversed completely by the addition of excess $Ca^{2+}$, whereas in the case of $Zn^{2+}$, it was necessary to add o-phenanthroline prior to $Ca^{2+}$.

Typical serine proteinase group-specific inhibitors have no effect on enzyme activity, and it is likely that inhibition by both TLCK and TPCK was caused by reaction with an essential cysteine residue in the enzyme, a known property of chloromethyl ketone derivatives. Significantly, Arg-gingipain-1 was inhibited by such cysteine proteinase inhibitors as trans-epoxysuccinyl-L-leucylamido-(4-guanidino)butane, leupeptin and antipain. Although the reactions were not stoichiometric, the inhibition was concentration-dependent. However, human cystatin C, an inhibitor of mammalian and plant cysteine proteinases, does not inhibit Arg-gingipain-1, nor did any of the trypsin-specific inhibitors from human plasma, including α2-macroglobulin, α1-proteinase inhibitor, antithrombin III, and α2-antiplasmin. Indeed, preliminary investigations actually suggested that the inhibitor in each case was being inactivated by Arg-gingipain-1.

TABLE 3

Effect of inhibitors on the amidolytic activity of Arg-gingipain-1

| Compound | Residual activity |
|---|---|
| Serine proteinase group-specific inhibitors | |
| Diisopropylfluorophosphate (10.0 mM) | 100.0 |

TABLE 3-continued

Effect of inhibitors on the amidolytic activity of Arg-gingipain-1

| Compound | Residual activity |
| --- | --- |
| Phenylmethylsulfonyl fluoride (10.0 mM) | 100.0 |
| 3,4-Dichloroisocoumarin (10.0 mM) | 100.0 |
| Cysteine proteinase group-specific inhibitors | |
| Iodoacetamide | |
| 1.0 mM | 67.6 |
| 10.0 mM | 0.0 |
| Iodoacetic acid | |
| 1.0 mM | 83.2 |
| 10.0 mM | 4.4 |
| N-Ethylmaleimide | |
| 1.0 mM | 79.5 |
| 10.0 mM | 3.0 |
| Chelating agents | |
| EDTA | |
| 1.0 mM | 18.6 |
| 10.0 mM | 1.8 |
| EGTA | |
| 1.0 mM | 21.3 |
| 10.0 mM | 2.4 |
| o-Phenanthroline (10.0 mM) | 95.7 |
| Others | |
| ZnCl$_2$ | |
| 1.0 mM | 90.0 |
| 10.0 mM | 0.6 |
| MgCl$_2$ (10.0 mM) | 100.0 |
| TLCK (1.0 mM) | 0.1 |
| TPCK (1.0 mM) | 0.1 |
| p-Aminobenzamidine (10.0 mM) | 13.7 |
| N-Chlorosuccinimide | |
| 1.0 mM | 20.0 |
| 10.0 mM | 1.5 |
| NaCl (0.16M) | 100.0 |

Calcium ion stabilizes Arg-gingipain-1 without directly affecting activity. With Ca$^{2+}$ present the enzyme is stable in the pH range between 4.5 and 7.5 for several days at 4° C. However, below pH 4.0 or in the absence of Ca$^{2+}$, enzyme activity is quickly lost. At 37° C. Ca$^{2+}$ considerably increases stability, although activity is lost more rapidly than at the lower temperature. At −20° C. Arg-gingipain-1 is stable for several months. During lyophilization, however, it irreversibly loses more than 90% of its catalytic activity.

The amidolytic activity of the purified Arg-gingipain-1 on synthetic peptide substrates was limited to substrates with a P$_1$-Arg residue. Even then Arg-gingipain-1 had significantly different turnover rates on individual substrates, being most effective against S-2238 and S-2222 (Table 4). This narrow specificity was confirmed by examination of the cleavage products after incubation with the insulin B chain or mellitin; it was found that cleavage occurred specifically after only Arg residues, but not after Lys or any other amino acids unless the last affinity chromatography step over L-Arginine-Sepharose 4B was omitted.

TABLE 4

Amidolytic activity of Arg-gingipain-1

| Substrate | Activity nmol/μg/h |
| --- | --- |
| D-Phe-Pip-Arg-pNA (S-2238) | 756.0 |
| Bz-Ile—Glu-(γ-OR)-Gly Arg-pNA (S-2222) | 614.0 |
| D-Ile—Pro—Arg-pNA (S-2288) | 315.0 |
| Bz-Arg-pNA | 293.0 |
| D-Val—Leu—Lys-pNA (S-2251) | 0.1 |
| Suc-Ala—Ala—Ala-pNA | 0 |
| MeO-Suc-Ala—Ala—Pro—Val-pNA | 0 |
| Suc-Ala—Ala—Pro—Phe-pNA | 0 |
| Gly—Pro-pNA | 0 |
| Cbz-Phe—Leu—Glu-pNA | 0 |

Preliminary studies indicated that the proteinase activity in each of the four pooled peaks, detected by assay for Bz-L-Arg-pNA hydrolysis after Sephadex G-150 chromatography, could not only digest arginine-specific synthetic substrates but also casein, collagen, the serpins α1-antichymotrypsin and antithrombin III, and the arginine-rich, neutrophil proteinase cathepsin G (but not human neutrophil elastase). In addition, enzymes in peak 1 could also degrade type I collagen and α1-proteinase inhibitor. However, no collagen degradation by purified Arg-gingipain-1 was ever detected.

Figure 3:
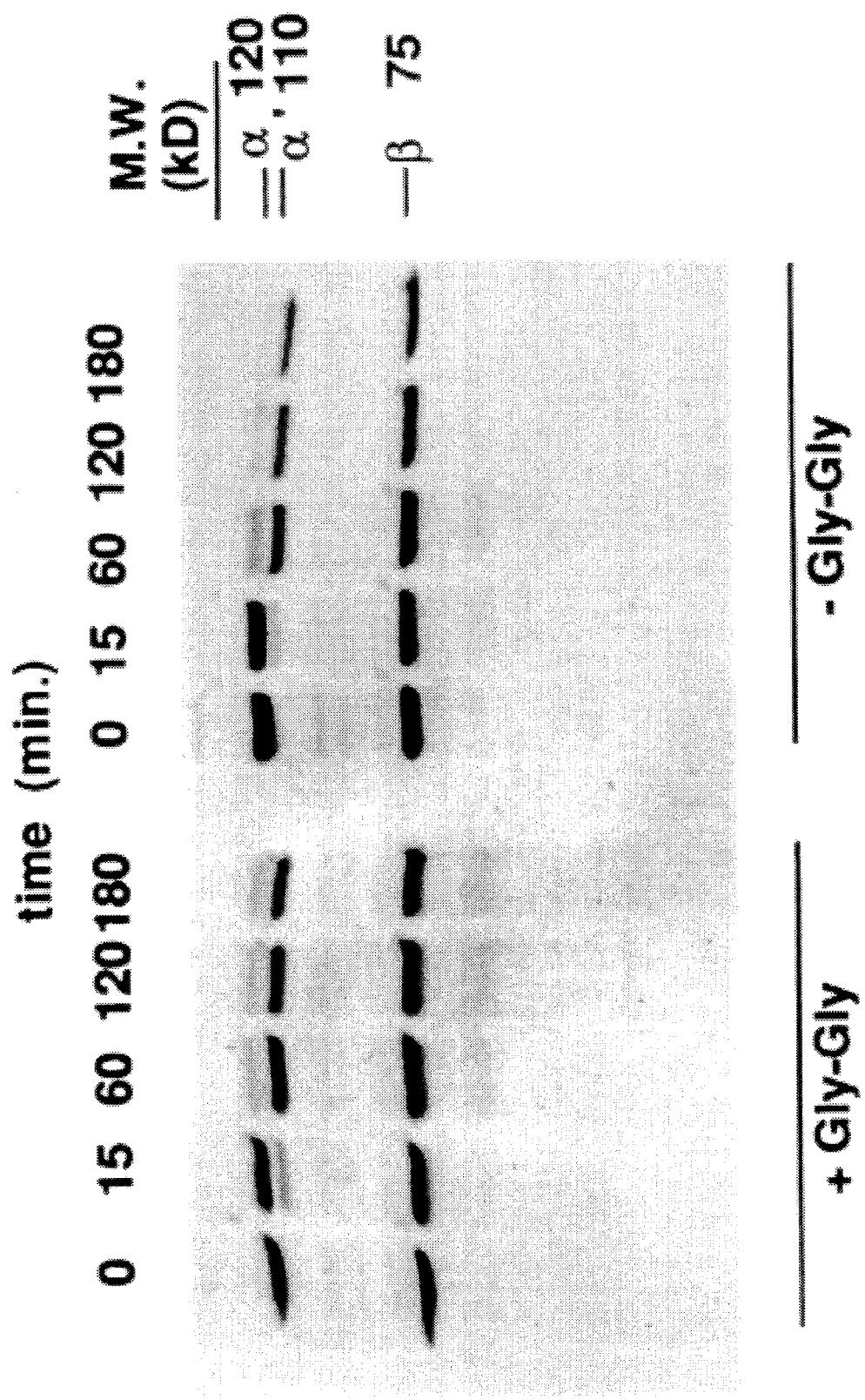
FIG. 3 is a photograph of a Coomassie Blue-stained SDS-polacrylamide gel (5–15% gradient) of human C3 treated with Arg-gingipain-1. Human C3 (13.3 µg) was treated at 37° C. with Arg-gingipain-1 (142 ng, 728 units) at a 1:25 mol to mol ratio. The 0.5 ml digestion mixture contained 10 mM Tris-HCl, 1 mM cysteine, 5 mM CaCl2, 50 mM gly-gly, pH 7.0. 45 µl aliquots were removed at designated times, and the digestion was stopped by adding TLCK to a final concentration of 2mM. SDS-PAGE was carried out under reducing conditions. The $\alpha$, $\alpha^1$ and $\beta$ C3 bands and corresponding molecular weights are labeled.

Because progressive periodontitis is characterized by tissue degradation, collagen destruction and a strong inflammatory response, and because P. gingivalis was known to exhibit complement-hydrolyzing activity, purified Arg-gingipain-1 was tested for proteinase activity using purified human complement C3 and C5 as substrates. Purified human C3 was digested with gingipain-1 at a molar ratio of 25:1 in digestion buffer. Since it has been shown that the enzyme cleaves substrates such as Bz-Arg-pNA more rapidly in the presence of glycyl-glycine (Gly-Gly), time course digests both in the presence and absence of the dipeptide were carried out. The cysteine proteinase selectively cleaved the α-chain, generating what initially appeared to be the α'-chain of C3b. This result indicates that a fragment approximately the size of C3a (i.e. 9 kDa) had been released (FIG. 3). The rate of digestion with Gly-Gly present appears only slightly more rapid than without the dipeptide. The C3 α-chain was nearly all converted to the α'-chain after 1 h of digestion. Further breakdown fragments of the C3 α'-chain were observed and a decreasing intensity of the α'-band suggested that degradation continues. Visual evidence suggested that the C3 β-chain is resistant to this proteinase whether Gly-Gly is present or not.

Attempts to demonstrate C3a biological activity in the C3 digestion mixture were unsuccessful. A digest containing 300 μg of C3 was applied to a guinea pig ileal strip with no response. The sensitivity of the ileum assay would have detected approximately 1% of the C3a potentially generated in the digest. When the C3 digest was resolved by SDS-polyacrylamide gel electrophoresis (13% gel) and developed with silver stain, no material was detected in the C3a region. Thus, the C3a-like fragment released from the α-chain was extensively degraded by gingipain-1.

Figure 4:
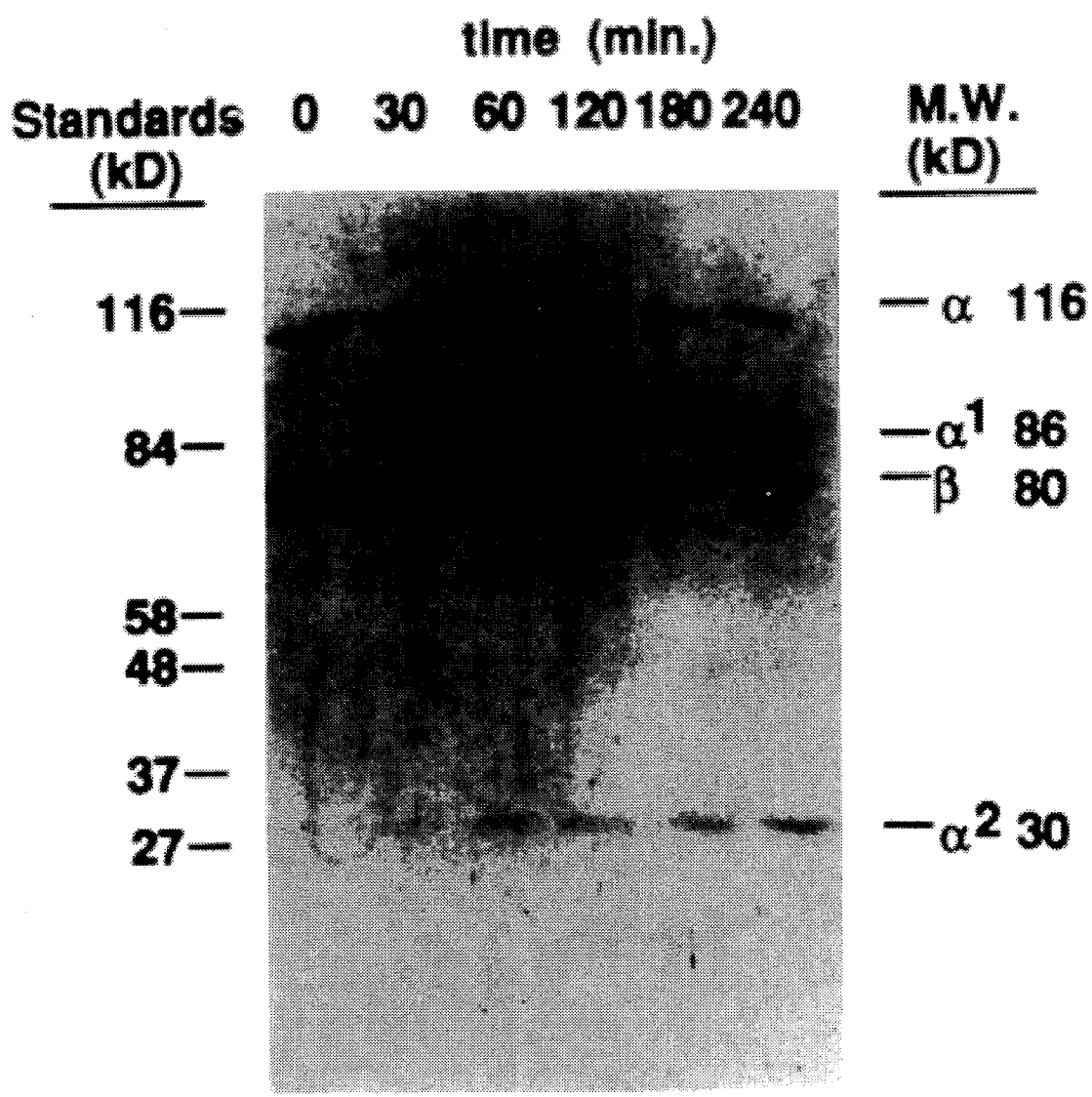
FIG. 4 is a photograph of a Coomassie Blue-stained SDS polyacrylamide gel (5–15% gradient) with aliquots of human C5 digested with Arg-gingipain-1 run under reducing conditions. Human C5 (16.2 g) was exposed to gingipain-1 (173 ng, specific activity 728 units) at 25:1 molar ratio. The 0.5 ml reaction also contained 10mM Tris-HCl, 1 mM cysteine, 5mM $CaCl_2$, pH 7.0. Aliquots were removed at the designated times, and the reaction was immediately inhibited by adding TLCK to a final concentration of 2 mM. The position of molecular weight standards and the $\alpha$, $\alpha^1$, $\beta$ and $\alpha^2$ C5 proteins are noted, together with the corresponding molecular weights.
Figure 5:
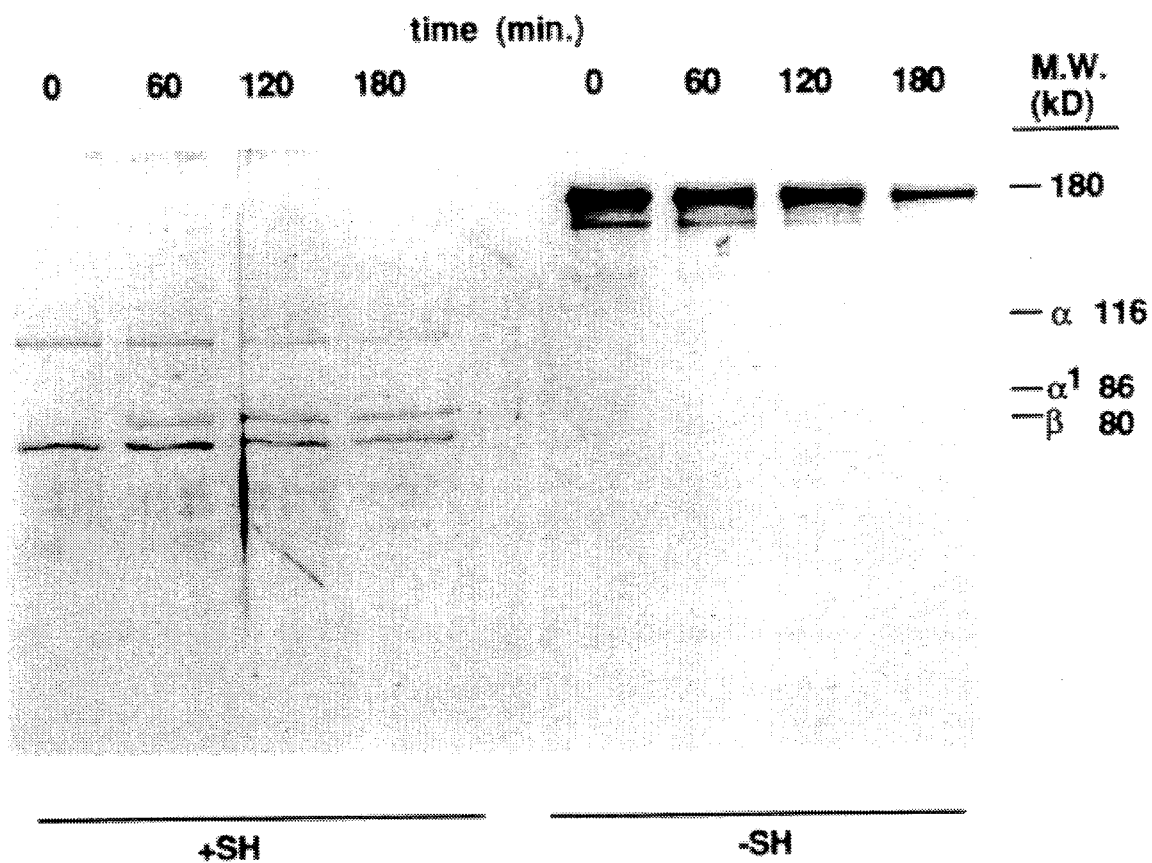
FIG. 5 is a photograph of an SDS-PAGE gel (8%, run under reducing conditions) with human C5 (9.4 µg) incubated with 100 ng Arg-gingipain-1 (specific activity 728 units, 50:1 molar ratio) in 0.5 ml digestion mixture, pH 7.0. 50 µl aliquots were removed at the designated times; proteolysis was inhibited by the addition of TLCK (2mM final concentration). Samples were heated at 100° C. for 5 min. in sample buffer with and without 1 mM cysteine before SDS-PAGE. The stained gel shows the cleavage of the $\alpha$-chain of C5a, as in the reduced gel (See FIG. 4). The unreduced material remained covalently intact after cleavage.

Human C5 was digested by Arg-gingipain-1 at a 25:1 molar ratio, and the degradation pattern obtained is shown in FIG. 4. Initial cleavage was specific for the C5 α-chain, as in the case of C3, except that the cleavage occurred internally generating fragments of 86 kDa (α-1) and 30 kDa (α-2), respectively. The dominant bands observed in SDS-PAGE gels after 1 h of digestion were the β-chain and the α-1 and α-2 fragments of C5. The amino-terminal sequences of the α-1 and α-2 fragments were determined as G-Y-G-D-S-N-Y-K (SEQ ID NO:2) and T-L-Q-K-K-I-E-E-I-A- (SEQ ID NO:3), respectively. The α-1 (86 kDa) and the α-2 (30 kDa) fragments were the first polypeptides to be formed from cleavage of C5 by gingipain-1, and they equal the molecular weight of the intact α-chain. Therefore the initial site of cleavage in the C5 α-chain occurred within an intrachain or interchain disulfide loop located near the carboxyl-terminal end of this polypeptide chain. According to the banding pattern of C5 digested under nonreducing conditions, the fragmented α-chain and intact β-chain remain covalently attached after limited digestion (FIG. 5). When a 13% SDS-PAGE gel of C5 after 2 and 3 h of digestion was stained with silver reagent, a band in the size range of C5a was observed.

Figure 6:
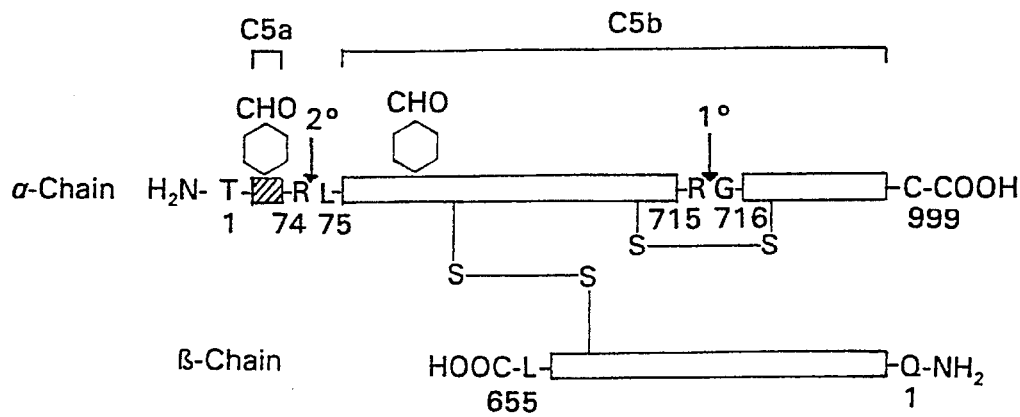

A scheme for the cleavage of C5 by Arg-gingipain-1 is shown in FIG. 6. The enzyme attacks primarily the α-chain of C5. The first peptide bond cleaved is between arginine 715 and glycine 716 of the α-chain. Subsequently, other sites are attacked including the bond between positions 74 and 75, which generates C5a.

Both human C3a and C5a were subjected to proteolysis by Arg-gingipain-1 (specific activity 1,123 units (per $A_{280}$) at 100:1 molar ratios, and degradation was evaluated after electrophoresis on cellulose acetate strips. C3a was extensively degraded after 30-min incubation, both in the presence and absence of Gly-Gly. In the presence of glycyl-glycine the C3a appeared partially degraded after 10 min and was nearly destroyed after 60 min. Cleavage of C3a by the Arg-gingipain-1 explains why activity could not be demonstrated in the C3 digestion mixtures; presumably the C3a fragment was released and then destroyed as the digestion continued.

C5a is more resistant to the Arg-gingipain-1 than C3a, based on the apparent rate of degradation. The majority of C5a remained intact even after 60 min of digestion, indicating that when C5 is subjected to prolonged digestion by Arg-gingipain-1, functional C5a may accumulate in the digestion mixture without further appreciable degradation.

Figure 7:
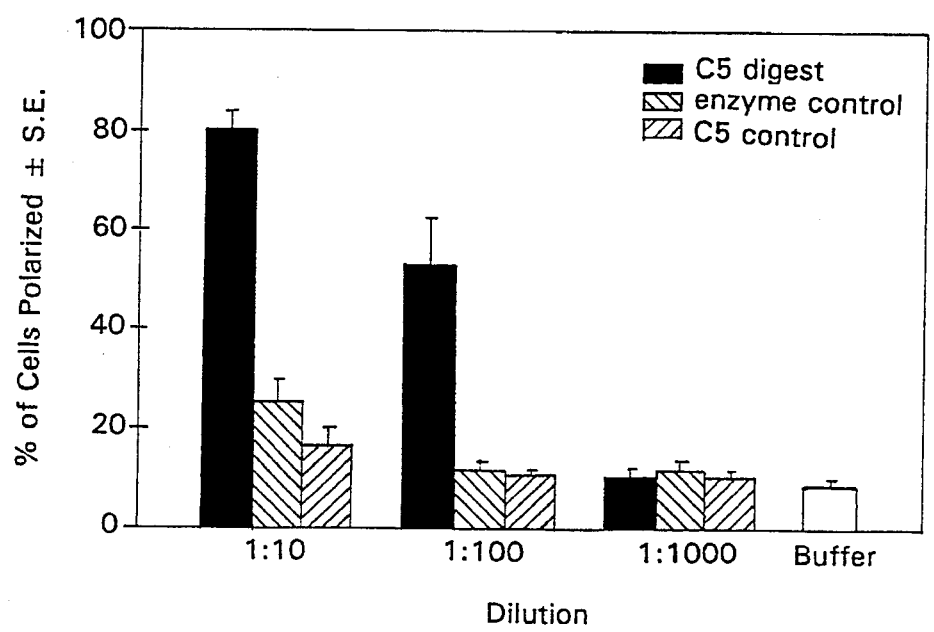
FIG. 7 illustrates the results of neutrophil polarization assays on dilutions of a human C5+Arg-gingipain-1 digestion mixture. 90 µg C5 was digested with Arg-gingipain-1 (specific activity 728 units, molar ratio 25:1) in 0.2 ml digestion buffer, pH 7.0, at 37° C. for 3 hours. Proteolysis was inhibited by adding TLCK to a final concentration of 2 mM. 50 µl EBSS containing 10 mM MOPS, pH 7.3 before dilutions were assayed for biological activity. Controls were the same except for lack of C5 (enzyme control) or Arg-gingipain (C5 control).
Figure 8:
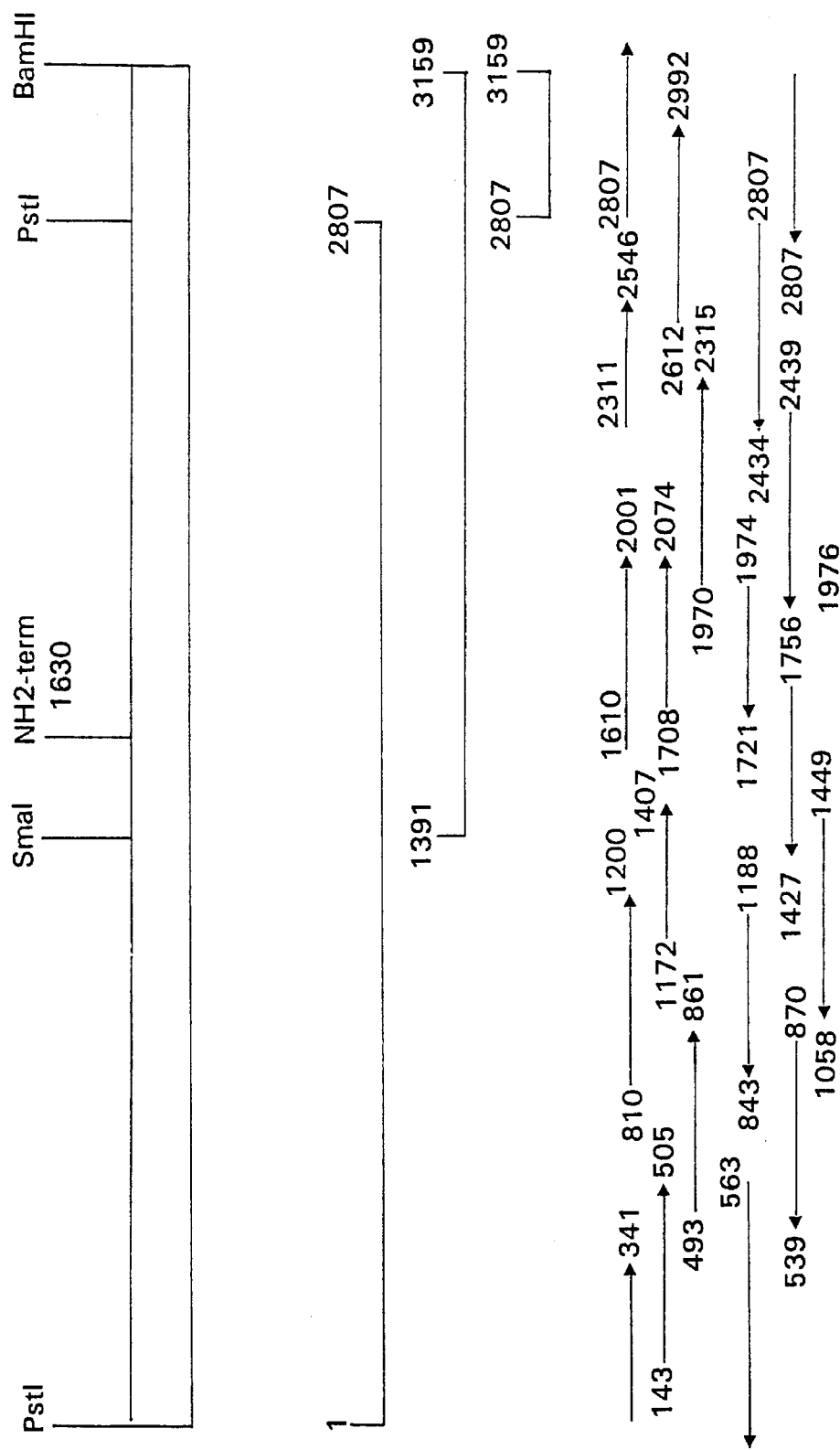
FIG. 8 illustrates the composite physical map of Arg-gingipain-2 DNA clones. The first codon of the mature gingipain is indicated. Clones PstI(1)/PstI(2807), SmaI(1391)/BamHI(3159), and PstI(2807)/BamHI(3159) are represented. The arrows indicate the extent and direction of sequencing. M13 primers and internal primers were used to sequence both strands of the putative gingipain-2 gene, initially as double strand sequencing on clone PstI(1)/PstI(2807) and then as single strand sequencing on PstI(1)/PstI(2807) clone and on PstI(2807)/BamHI(3159) clone in both directions. The junction PstI(2807) was sequenced on double stranded clone SmaI(1391)/BamHI(3159). Only restriction sites employed in cloning are indicated.

C5a biological activity was detected as follows. Human C5 was digested at a molar ratio of 25:1 (728 U preparation) for three hours. Aliquots of the digestion mixture were diluted and incubated with human neutrophils. Characteristic morphologic changes in the cells, known as polarization, were scored by counting deformed cells relative to normally rounded cells. The neutrophil response to the digestion mixture indicated that a factor with activity like that of C5a was present (FIG. 7). Calculations of the activity expressed by the C5 digest ($ED_{50}$ for a 1:100 dilution) compared with purified C5a (described in Ember et al. (1992) *J. Immunol.* 148, 3165–3173) indicated that approximately 25% of the potential C5a activity had been generated.

A C5 digest was prepared for the neutrophil chemotaxis assay using the Arg-gingipain-1 preparation with a somewhat higher specific activity (1,123 units) than previous preparations and was used at a 100:1 molar ratio. Aliquots of the digestion mixture were diluted, and neutrophil migration was evaluation using a modified Boyden chamber assay. Estimates of the recovery of activity relative to purified C5a indicated a yield of 20%.

To characterize the bioactive products of Arg-gingipain-1 cleavage of C5, a C5 digest containing $^{125}$I-C5a added after digestion was gel size fractimated on a Bio-Gel P-60 column. An early peak of material eluted at the C5 position, and the broad second peak eluted where fragments the size of C5a would elute. Both pooled fractions of the higher molecular weight and the lower molecular weight materials were tested for neutrophil polarization and chemotactic activity. Only the pooled material of lower molecular weight; of sizes similar to C5a, elicited the polarization response and cellular migratory response.

To test for in vivo biological activity of Arg-gingipain-1, the purified enzyme was injected into guinea pig skin. Arg-gingipain-1 induced vascular permeability enhancement at concentrations greater than $10^{-8}$M in dose-dependent and proteolytic activity dependent manners. The vascular permeability enhancement of Arg-gingipain-1 peaked in 15 min. after injection and almost vanished in 60 min. in the guinea pig skin assay.

The vascular permeability enhancement activity of Arg-gingipain-1 was not inhibited by diphenhydramine (an antihistamine), but the activity was enhanced by SQ 20,881 (angiotensin-converting enzyme inhibitor). The vascular permeability enhancement by Arg-gingipain-1 was inhibited by soybean trypsin inhibitor (SBTI) at a concentration of $10^{-5}$M, a concentration at which SBTI did not inhibit enzymatic activity, as measured with Bz-L-Arg-pNA and azocasein as the substrates.

Human plasma or guinea pig plasma treated with Arg-gingipain-1 ($10^{-8}$ to $10^{-6}$M) induced vascular permeability enhancement in the guinea pig skin assay. Vascular permeability enhancement by Arg-gingipain-1 treated plasma was increased by addition of 1,10-phenanthroline (kininase inhibitor, chelating agent for Zn ions) to a final concentration of 1 mM. Vascular permeability enhancement by Arg-gingipain-1 treated plasmas was markedly reduced when plasmas deficient in Hageman factor, prekallikrein or high molecular weight kininogen were used. These results indicate that vascular permeabilizing enhancement by Arg-gingipain-1 acts via activation of Hageman factor and the subsequent release of bradykinin from high molecular weight kininogen by kallikrein.

It was also determined that intradermal injection of Arg-gingipain-1 in the guinea pig resulted in neutrophil accumulation at the site of injection. Peak accumulation was at 6 hour post-injection. This activity was dependent on proteolytic activity of the Arg-gingipain-1 protein.

The foregoing results demonstrate the ability of Arg-gingipain-1 to elicit inflammatory responses in a guinea pig animal model.

Arg-gingipain-1 may be used in methods of identifying agents that modulate Arg-gingipain proteinase activity, whether by acting on the proteinase itself or preventing the interaction of a proteinase with a protein in gingival area, such as C3 or C5. One such method comprises the steps of incubating a proteinase with a putative therapeutic, i.e., Arg-gingipain-1 inhibiting, agent; determining the activity of the proteinase incubated with the agent; and comparing the activity obtained in step with the activity of a control sample of proteinase that has not been incubated with the agent.

SDS-PAGE analysis of the purified high molecular weight form of Arg-gingipain, without boiling, revealed a single band of apparent molecular mass of 95 kDa. This estimate was confirmed by analytical chromatography over a TSK 3000SW gel filtration column. When the enzyme preparation was boiled before SDS-PAGE, however, bands of apparent molecular masses of 50 kDa, 43 kDa, 27 kDa and 17 kDa were observed. These bands were not generated by treatments at temperatures below boiling, by reducing agents or detergents. It was concluded that the 95 kDa band was the result of strong non-covalent binding between the lower molecular weight proteins.

The 50 kDa component of the high molecular weight Arg-gingipain was characterized with respect to N-terminal amino acid sequence over 22 amino acids. The sequence was identical to the first 22 amino acids of the 50 kDa, low molecular weight Arg-gingipain-1. Characterization of the high molecular weight Arg-gingipain activity showed the same dependence on cysteine (or other thiols) and the same spectrum of response to potential inhibitors. Although the high molecular weight Arg-gingipain was stimulated by glycine compounds, the response was only about half that observed for the low molecular weight form.

Methods of treating or ameliorating the effects of Arg-gingipain-1 on affected gingival crevices of a human or animal with periodontal disease are provided. Such methods include administering to the animal (or human) an effective amount of a physiologically acceptable Arg-gingipain-1 inhibitor. Known proteinase inhibitors are generally not physiologically acceptable, but acceptable inhibitors will include agents that inhibit Arg-gingipain-1 but do not affect, or affect only marginally, the activity of endogenous proteinases. Such inhibitors can be obtained from a variety of sources including but not limited to inhibitory antibodies and small molecules. The inhibitors can be administered by a variety of methods including but not limited to topically, via aerosol to the nasal passages or lungs, subdermally and intravenously. The inhibitors can be administered as needed, particularly when applied topically. These methods of administration are known in the art and will not be described in detail herein.

The primary structure of the $NH_2$-terminus of Arg-gingipain-1 determined by direct amino acid sequencing. (SEQ ID NO:1) was used to prepare a mixture of synthetic primer oligonucleotides GIN-1-32 (SEQ ID NO:7) coding for amino acids 2 to 8 of the mature protein and primer GIN-2-30 (SEQ ID NO:8) coding for amino acids 25–32 of the mature protein. These primers were used in PCR on P. gingivalis DNA. A single 105-base pair product (P105) resulted. This was cloned into pCR-Script™SK(−) (Stratagene) and sequenced. Sequence analysis of P105 generated 49 nucleotides from an Arg-gingipain coding sequence. On the basis of the sequence of P105, another primer (GIN-8S-48) SEQ ID NO:9 corresponding to the coding strand of the partial Arg-gingipain gene (48-mers) was synthesized in order to screen the λDASH DNA library using a $^{32}$P-labeled GIN-8S-48 probe. A partial sequence of the Arg-gingipain gene (nucleotides 1–3159, SEQ ID NO:4) was determined by screening the P. gingivalis DNA library using $^{32}$P-labeled hybridization GIN-8S-48 probe (SEQ ID NO:9). From a total of $2 \times 10^5$ independent plaques screened, seven positive clones were isolated and purified. After extraction and purification, the DNA was analyzed by restriction enzymes: One clone (A1) has a 3.5 kb BamHI fragment and a 3 kb PstI fragment; another clone (B1) has a 9.4 kb BamHI fragment and a 9.4 kb PstI fragment; and 5 clones have a 9.4 kb BamHI fragment and a 10 kb PstI fragment. These results are similar to those obtained by Southern analysis of P. gingivalis DNA and are consistent with the existence of at least two Arg-gingipain genes. The A1 clone was chosen for sequencing because the expected DNA size to encode a 50-KDa protein is approximately 1.35 kb. The 3.159 kb PstI/BamHI fragment from clone A1 was subsequently subcloned into pbluescript SK(−) as a PstI fragment and a SmaI/BamHI fragment and into M13mp18 and 19 as a PstI fragment and a PstI/BamHI fragment and sequenced. In order to clone the stop codon of gingipain-1, which was missing in the PstI/BamHI fragment, PstI/HindIII double digested P. gingivalis DNA clones were hybridized with $^{32}$P-labeled GIN-14-20 (nucleotides 2911–2930) localized at the 3' end of this clone. A PstI/HindIII fragment of approximately 4.3 kb was identified and cloned into pbluescript SK(−). A smaller fragment (PstI/Asp713) was also subcloned into M13mp18 and 19.

SEQ ID NO:4 is the DNA sequence of the 3159 bp PstI/BamHI fragment (see Table 5).

TABLE 5

Nucleotide sequence and deduced
amino acid sequence of Gingipain-1

```
         10            20            30            40
          *             *             *             *
CTG CAG AGG GCT GGT AAA GAC CGC CTC GGG ATC GAG GCC AAA GAG ACG
GAC GTC TCC CGA CCA TTT CTG GCG GAG CCC TAG CTC CGG TTT CTC TGC 50            60            70            80            90
  *             *             *             *             *
GGC ACA AGC CGC CGC AGC CTC CTC TTC GAA GGT GTC TCG AAC GTC CAC
CCG TGT TCG GCG GCG TCG GAG GAG AAG CTT CCA CAG AGC TTG CAG GTG 100           110           120           130           140
  *             *             *             *             *
ATC GGT GAA TCC GTA GCA GTG CTC ATT GCC ATT GAG CAG CAC CGA GGT
TAG CCA CTT AGG CAT CGT CAC GAG TAA CGG TAA CTC GTC GTG GCT CCA 150           160           170           180           190
  *             *             *             *             *
GTG GCG CAT CAG ATA TAT TTT CAT CAG TGG ATT ATT AGG GTA TCG GTC
CAC CGC GTA GTC TAT ATA AAA GTA GTC ACC TAA TAA TCC CAT AGC CAG 200           210           220           230           240
  *             *             *             *             *
AGA AAA AGC CTT CCG AAT CCG ACA AAG ATA GTA GAA AGA GAG TGC ATC
TCT TTT TCG GAA GGC TTA GGC TGT TTC TAT CAT CTT TCT CTC ACG TAG 250           260           270           280
        *             *             *             *
TGA AAA CAG ATC ATT CGA GGA TTA TCG ATC AAC TGA AAA GGC AGG AGT
ACT TTT GTC TAG TAA GCT CCT AAT AGC TAG TTG ACT TTT CCG TCC TCA
```

TABLE 5-continued

Nucleotide sequence and deduced amino acid sequence of Gingipain-1

```
         290         300         310         320         330
          *           *           *           *           *
TGT TTT GCG TTT TGG TTC GGA AAA TTA CCT GAT CAG CAT TCG TAA AAA
ACA AAA CGC AAA ACC AAG CCT TTT AAT GGA CTA GTC GTA AGC ATT TTT 340         350         360         370         380
          *           *           *           *           *
CGT GGC GCG AGA ATT TTT TCG TTT TGG CGC GAG AAT TAA AAA TTT TTG
GCA CCG CGC TCT TAA AAA AGC AAA ACC GCG CTC TTA ATT TTT AAA AAC 390         400         410         420         430
          *           *           *           *           *
GAA CCA CAG CGA AAA AAA TCT CGC GCC GTT TTC TCA GGA TTT ACA GAC
CTT GGT GTC GCT TTT TTT AGA GCG CGG CAA AAG AGT CCT AAA TGT CTG 440         450         460         470         480
          *           *           *           *           *
CAC AAT CCG AGC ATT TTC GGT TCG TAA TTC ATC GAA GAG ACA GGT TTT
GTG TTA GGC TCG TAA AAG CCA AGC ATT AAG TAG CTT CTC TGT CCA AAA 490         500         510         520
                      *           *           *           *
ACC GCA TTG AAA TCA GAG AGA GAA TAT CCG TAG TCC AAC GGT TCA TCC
TGG CGT AAC TTT AGT CTC TCT CTT ATA GGC ATC AGG TTG CCA AGT AGG 530         540         550         560         570
   *           *           *           *           *
TTA TAT CAG AGG TTA AAA GAT ATG GTA CGC TCA TCG AGG AGC TGA TTG
AAT ATA GTC TCC AAT TTT CTA TAC CAT GCG AGT AGC TCC TCG ACT AAC 580         590         600         610         620
          *           *           *           *           *
GCT TAG TAG GTG AGA CTT TCT TAA GAG ACT ATC GGC ACC TAC AGG AAG
CGA ATC ATC CAC TCT GAA AGA ATT CTC TGA TAG CCG TGG ATG TCC TTC 630         640         650         660         670
          *           *           *           *           *
TTC ATG GCA CAC AAG GCA AAG GAG GCA ATC TTC GCA GAC CGG ACT CAT
AAG TAC CGT GTG TTC CGT TTC CTC CGT TAG AAG CGT CTG GCC TGA GTA 680         690         700         710         720
          *           *           *           *           *
ATC AAA AGG ATG AAA CGA CTT TTC CAT ACG ACA ACC AAA TAG CCG TCT
TAG TTT TCC TAC TTT GCT GAA AAG GTA TGC TGT TGG TTT ATC GGC AGA 730         740         750         760
                      *           *           *           *
ACG GTA GAC GAA TGC AAA CCC AAT ATG AGG CCA TCA ATC AAT CCG AAT
TGC CAT CTG CTT ACG TTT GGG TTA TAC TCC GGT AGT AG TTA GGC TTA 770         780         790         800         810
   *           *           *           *           *
GAC AGC TTT TGG GCA ATA TAT TAT GCA TAT TTT GAT TCG CGT TTA AAG
CTG TCG AAA ACC CGT TAT ATA ATA CGT ATA AAA CTA AGC GCA AAT TTC 820         830         840         850         860
          *           *           *           *           *
GAA AAG TGC ATA TAT TTG CGA TTG TGG TAT TTC TTT CGG TTT CTA TGT
CTT TTC ACG TAT ATA AAC GCT AAC ACC ATA AAG AAA GCC AAA GAT ACA 870         880         890         900         910
          *           *           *           *           *
GAA TTT TGT CTC CCA AGA AGA CTT TAT AAT GCA TAA ATA CAG AAG GGG
CTT AAA ACA GAG GGT TCT TCT GAA ATA TTA CGT ATT TAT GTC TTC CCC 920         930         940         950         960
                      *           *           *           *           *
TAC TAC ACA GTA AAA TCA TAT TCT AAT TTC ATC AAA ATG AAA AAC TTG
ATG ATG TGT CAT TTT AGT ATA AGA TTA AAG TAG TTT TAC TTT TTG AAC
                                                      M   K   N   L 970         980         990         1000
               *           *           *           *
AAC AAG TTT GTT TCG ATT GCT CTT TGC TCT TCC TTA TTA GGA GGA ATG
TTG TTC AAA CAA AGC TAA CGA GAA ACG AGA AGG AAT AAT CCT CCT TAC
 N   K   F   V   S   I   A   L   C   S   S   L   L   G   G   M
```

TABLE 5-continued

Nucleotide sequence and deduced
amino acid sequence of Gingipain-1

```
1010            1020            1030            1040            1050
 *               *               *               *               *
GCA TTT GCG CAG CAG ACA GAG TTG GGA CGC AAT CCG AAT GTC AGA TTG
CGT AAA CGC GTC GTC TGT CTC AAC CCT GCG TTA GGC TTA CAG TCT AAC
 A   F   A   Q   Q   T   E   L   G   R   N   P   N   V   R   L 1060            1070            1080            1090            1100
        *               *               *               *               *
    CTC GAA TCC ACT CAG CAA TCG GTG ACA AAG GTT CAG TTC CGT ATG GAC
    GAG CTT AGG TGA GTC GTT AGC CAC TGT TTC CAA GTC AAG GCA TAC CTG
     L   E   S   T   Q   Q   S   V   T   K   V   Q   F   R   M   D 1110            1120            1130            1140            1150
             *               *               *               *               *
        AAC CTC AAG TTC ACC GAA GTT CAA ACC CCT AAG GGA ATC GGA CAA GTG
        TTG GAG TTC AAG TGG CTT CAA GTT TGG GGA TTC CCT TAG CCT GTT CAC
         N   L   K   F   T   E   V   Q   T   P   K   G   I   G   Q   V 1160            1170            1180            1190            1200
                 *               *               *               *               *
            CCG ACC TAT ACA GAA GGG GTT AAT CTT TCC GAA AAA GGG ATG CCT ACG
            GGC TGG ATA TGT CTT CCC CAA TTA GAA AGG CTT TTT CCC TAC GGA TGC
             P   T   Y   T   E   G   V   N   L   S   E   K   G   M   P   T 1210            1220            1230            1240
                     *               *               *               *
                CTT CCC ATT CTA TCA CGC TCT TTG GCG GTT TCA GAC ACT CGT GAG ATG
                GAA GGG TAA GAT AGT GCG AGA AAC CGC CAA AGT CTG TGA GCA CTC TAC
                 L   P   I   L   S   R   S   L   A   V   S   D   T   R   E   M 1250            1260            1270            1280            1290
 *               *               *               *               *
AAG GTA GAG GTT GTT TCC TCA AAG TTC ATC GAA AAG AAA AAT GTC CTG
TTC CAT CTC CAA CAA AGG AGT TTC AAG TAG CTT TTC TTT TTA CAG GAC
 K   V   E   V   V   S   S   K   F   I   E   K   K   N   V   L 1300            1310            1320            1330            1340
     *               *               *               *               *
ATT GCA CCC TCC AAG GGC ATG ATT ATG CGT AAC GAA GAT CCG AAA AAG
TAA CGT GGG AGG TTC CCG TAC TAA TAC GCA TTG CTT CTA GGC TTT TTC
 I   A   P   S   K   G   M   I   M   R   N   E   D   P   K   K 1350            1360            1370            1380            1390
         *               *               *               *               *
    ATC CCT TAC GTT TAT GGA AAG AGC TAC TCG CAA AAC AAA TTC TTC CCG
    TAG GGA ATG CAA ATA CCT TTC TCG ATG AGC GTT TTG TTT AAG AAG GGC
     I   P   Y   V   Y   G   K   S   Y   S   Q   N   K   F   F   P 1400            1410            1420            1430            1440
             *               *               *               *               *
        GGA GAG ATC GCC ACG CTT GAT GAT CCT TTT ATC CTT CGT GAT GTG CGT
        CCT CTC TAG CGG TGC GAA CTA CTA GGA AAA TAG GAA GCA CTA CAC GCA
         G   E   I   A   T   L   D   D   P   F   I   L   R   D   V   R 1450            1460            1470            1480
                     *               *               *               *
                GGA CAG GTT GTA AAC TTT GCG CCT TTG CAG TAT AAC CCT GTG ACA AAG
                CCT GTC CAA CAT TTG AAA CGC GGA AAC GTC ATA TTG GGA CAC TGT TTC
                 G   Q   V   V   N   F   A   P   L   Q   Y   N   P   V   T   K 1490            1500            1510            1520            1530
 *               *               *               *               *
ACG TTG CGC ATC TAT ACG GAA ATC ACT GTG GCA GTG AGC GAA ACT TCG
TGC AAC GCG TAG ATA TGC CTT TAG TGA CAC CGT CAC TCG CTT TGA AGC
 T   L   R   I   Y   T   E   I   T   V   A   V   S   E   T   S 1540            1550            1560            1570            1580
     *               *               *               *               *
GAA CAA GGC AAA AAT ATT CTG AAC AAG AAA GGT ACA TTT GCC GGC TTT
CTT GTT CCG TTT TTA TAA GAC TTG TTC TTT CCA TGT AAA CGG CCG AAA
 E   Q   G   K   N   I   L   N   K   K   G   T   F   A   G   F 1590            1600            1610            1620            1630
         *               *               *               *               *
    GAA GAC ACA TAC AAG CGC ATG TTC ATG AAC TAC GAG CCG GGG CGT TAC
    CTT CTG TGT ATG TTC GCG TAC AAG TAC TTG ATG CTC GGC CCC GCA ATG
     E   D   T   Y   K   R   M   F   M   N   Y   E   P   G   R   Y̲
```

TABLE 5-continued

Nucleotide sequence and deduced amino acid sequence of Gingipain-1

```
        1640          1650          1660          1670          1680
         *             *             *             *             *
ACA CCG GTA GAG GAA AAA CAA AAT GGT CGT ATG ATC GTC ATC GTA GCC
TGT GGC CAT CTC CTT TTT GTT TTA CCA GCA TAC TAG CAG TAG CAT CGG
 T   P   V   E   E   K   Q   N   G   R   M   I   V   I   V   A 1690          1700          1710          1720
            *             *             *             *
AAA AAG TAT GAG GGA GAT ATT AAA GAT TTC GTT GAT TGG AAA AAC CAA
TTT TTC ATA CTC CCT CTA TAA TTT CTA AAG CAA CTA ACC TTT TTG GTT
 K   K   Y   E   G   D   I   K   D   F   V   D   W   K   N   Q 1730          1740          1750          1760          1770
  *             *             *             *             *
CGC GGT CTC CGT ACC GAG GTG AAA GTG GCA GAA GAT ATT GCT TCT CCC
GCG CCA GAG GCA TGG CTC CAC TTT CAC CGT CTT CTA TAA CGA AGA GGG
 R   G   L   R   T   E   V   K   V   A   E   D   I   A   S   P 1780          1790          1800          1810          1820
       *             *             *             *             *
GTT ACA GCT AAT GCT ATT CAG CAG TTC GTT AAG CAA GAA TAC GAG AAA
CAA TGT CGA TTA CGA TAA GTC GTC AAG CAA TTC GTT CTT ATG CTC TTT
 V   T   A   N   A   I   Q   Q   F   V   K   Q   E   Y   E   K 1830          1840          1850          1860          1870
         *             *             *             *             *
GAA GGT AAT GAT TTG ACC TAT GTT CTT TTG GTT GGC GAT CAC AAA GAT
CTT CCA TTA CTA AAC TGG ATA CAA GAA AAC CAA CCG CTA GTG TTT CTA
 E   G   N   D   L   T   Y   V   L   L   V   G   D   H   K   D 1880          1890          1900          1910          1920
          *             *             *             *             *
ATT CCT GCC AAA ATT ACT CCG GGG ATC AAA TCC GAC CAG GTA TAT GGA
TAA GGA CGG TTT TAA TGA GGC CCC TAG TTT AGG CTG GTC CAT ATA CCT
 I   P   A   K   I   T   P   G   I   K   S   D   Q   V   Y   G 1930          1940          1950          1960
            *             *             *             *
CAA ATA GTA GGT AAT GAC CAC TAC AAC GAA GTC TTC ATC GGT CGT TTC
GTT TAT CAT CCA TTA CTG GTG ATG TTG CTT CAG AAG TAG CCA GCA AAG
 Q   I   V   G   N   D   H   Y   N   E   V   F   I   G   R   F 1970          1980          1990          2000          2010
  *             *             *             *             *
TCA TGT GAG AGC AAA GAG GAT CTG AAG ACA CAA ATC GAT CGG ACT ATT
AGT ACA CTC TCG TTT CTC CTA GAC TTC TGT GTT TAG CTA GCC TGA TAA
 S   C   E   S   K   E   D   L   K   T   Q   I   D   R   T   I 2020          2030          2040          2050          2060
      *             *             *             *             *
CAC TAT GAG CGC AAT ATA ACC ACG GAA GAC AAA TGG CTC GGT CAG GCT
GTG ATA CTC GCG TTA TAT TGG TGC CTT CTG TTT ACC GAG CCA GTC CGA
 H   Y   E   R   N   I   T   T   E   D   K   W   L   G   Q   A 2070          2080          2090          2100          2110
         *             *             *             *             *
CTT TGT ATT GCT TCG GCT GAA GGA GGC CCA TCC GCA GAC AAT GGT GAA
GAA ACA TAA CGA AGC CGA CTT CCT CCG GGT AGG CGT CTG TTA CCA CTT
 L   C   I   A   S   A   E   G   G   P   S   A   D   N   G   E 2120          2130          2140          2150          2160
             *             *             *             *             *
AGT GAT ATC CAG CAT GAG AAT GTA ATC GCC AAT CTG CTT ACC CAG TAT
TCA CTA TAG GTC GTA CTC TTA CAT TAG CGG TTA GAC GAA TGG GTC ATA
 S   D   I   Q   H   E   N   V   I   A   N   L   L   T   Q   Y 2170          2180          2190          2200
                *             *             *             *
GGC TAT ACC AAG ATT ATC AAA TGT TAT GAT CCG GGA GTA ACT CCT AAA
CCG ATA TGG TTC TAA TAG TTT ACA ATA CTA GGC CCT CAT TGA GGA TTT
 G   Y   T   K   I   I   K   C   Y   D   P   G   V   T   P   K
```

TABLE 5-continued

Nucleotide sequence and deduced
amino acid sequence of Gingipain-1

```
     2210          2220          2230          2240          2250
       *             *             *             *             *
AAC ATT ATT GAT GCT TTC AAC GGA GGA ATC TCG TTG GTC AAC TAT ACG
TTG TAA TAA CTA CGA AAG TTG CCT CCT TAG AGC AAC CAG TTG ATA TGC
 N   I   I   D   A   F   N   G   G   I   S   L   V   N   Y   T 2260          2270          2280          2290          2300
       *             *             *             *             *
GGC CAC GGT AGC GAA ACA GCT TGG GGT ACG TCT CAC TTC GGC ACC ACT
CCG GTG CCA TCG CTT TGT CGA ACC CCA TGC AGA GTG AAG CCG TGG TGA
 G   H   G   S   E   T   A   W   G   T   S   H   F   G   T   T 2310          2320          2330          2340          2350
       *             *             *             *             *
CAT GTG AAG CAG CTT ACC AAC AGC AAC CAG CTA CCG TTT ATT TTC GAC
GTA CAC TTC GTC GAA TGG TTG TCG TTG GTC GAT GGC AAA TAA AAG CTG
 H   V   K   Q   L   T   N   S   N   Q   L   P   F   I   F   D 2360          2370          2380          2390          2400
       *             *             *             *             *
GTA GCT TGT GTG AAT GGC GAT TTC CTA TTC AGC ATG CCT TGC TTC GCA
CAT CGA ACA CAC TTA CCG CTA AAG GAT AAG TCG TAC GGA ACG AAG CGT
 V   A   C   V   N   G   D   F   L   F   S   M   P   C   F   A 2410          2420          2430          2440
             *             *             *             *
GAA GCC CTG ATG CGT GCA CAA AAA GAT GGT AAG CCG ACA GGT ACT GTT
CTT CGG GAC TAC GCA CGT GTT TTT CTA CCA TTC GGC TGT CCA TGA CAA
 E   A   L   M   R   A   Q   K   D   G   K   P   T   G   T   V 2450          2460          2470          2480          2490
  *             *             *             *             *
GCT ATC ATA GCG TCT ACG ATC AAC CAG TCT TGG GCT TCT CCT ATG CGC
CGA TAG TAT CGC AGA TGC TAG TTG GTC AGA ACC CGA AGA GGA TAC GCG
 A   I   I   A   S   T   I   N   Q   S   W   A   S   P   M   R 2500          2510          2520          2530          2540
  *             *             *             *             *
GGG CAG GAT GAG ATG AAC GAA ATT CTG TGC GAA AAA CAC CCG AAC AAC
CCC GTC CTA CTC TAC TTG CTT TAA GAC ACG CTT TTT GTG GGC TTG TTG
 G   Q   D   E   M   N   E   I   L   C   E   K   H   P   N   N 2550          2560          2570          2580          2590
       *             *             *             *             *
ATC AAG CGT ACT TTC GGT GGT GTC ACC ATG AAC GGT ATG TTT GCT ATG
TAG TTC GCA TGA AAG CCA CCA CAG TGG TAC TTG CCA TAC AAA CGA TAC
 I   K   R   T   F   G   G   V   T   M   N   G   M   F   A   M 2600          2610          2620          2630          2640
             *             *             *             *             *
GTG GAA AAG TAT AAA AAG GAT GGT GAG AAG ATG CTC GAC ACA TGG ACT
CAC CTT TTC ATA TTT TTC CTA CCA CTC TTC TAC GAG CTG TGT ACC TGA
 V   E   K   Y   K   K   D   G   E   K   M   L   D   T   W   T 2650          2660          2670          2680
                   *             *             *             *
GTT TTC GGC GAC CCC TCG CTG CTC GTT CGT ACA CTT GTC CCG ACC AAA
CAA AAG CCG CTG GGG AGC GAC GAG CAA GCA TGT GAA CAG GGC TGG TTT
 V   F   G   D   P   S   L   L   V   R   T   L   V   P   T   K 2690          2700          2710          2720          2730
  *             *             *             *             *
ATG CAG GTT ACG GCT CCG GCT CAG ATT AAT TTG ACG GAT GCT TCA GTC
TAC GTC CAA TGC CGA GGC CGA GTC TAA TTA AAC TGC CTA CGA AGT CAG
 M   Q   V   T   A   P   A   Q   I   N   L   T   D   A   S   V 2740          2750          2760          2770          2780
       *             *             *             *             *
AAC GTA TCT TGC GAT TAT AAT GGT GCT ATT GCT ACC ATT TCA GCC AAT
TTG CAT AGA ACG CTA ATA TTA CCA CGA TAA CGA TGG TAA AGT CGG TTA
 N   V   S   C   D   Y   N   G   A   I   A   T   I   S   A   N
             ‾   ‾

2790          2800          2810          2820          2830
             *             *             *             *             *
GGA AAG ATG TTC GGT TCT GCA GTT GTC GAA AAT GGA ACA GCT ACA ATC
CCT TTC TAC AAG CCA AGA CGT CAA CAG CTT TTA CCT TGT CGA TGT TAG
 G   K   M   F   G   S   A   V   V   E   N   G   T   A   T   I
```

TABLE 5-continued

Nucleotide sequence and deduced amino acid sequence of Gingipain-1

```
              2840          2850          2860          2870          2880
               *             *             *             *             *
AAT CTG ACA GGT CTG ACA AAT GAA AGC ACG CTT ACC CTT ACA GTA GTT
TTA GAC TGT CCA GAC TGT TTA CTT TCG TGC GAA TGG GAA TGT CAT CAA
 N   L   T   G   L   T   N   E   S   T   L   T   L   T   V   V 2890          2900          2910          2920
               *             *             *             *
GGT TAC AAC AAA GAG ACG GTT ATT AAG ACC ATC AAC ACT AAT GGT GAG
CCA ATG TTG TTT CTC TGC CAA TAA TTC TGG TAG TTG TGA TTA CCA CTC
 G   Y   N   K   E   T   V   I   K   T   I   N   T   N   G   E 2930          2940          2950          2960          2970
 *             *             *             *             *
CCT AAC CCC TAC CAG CCC GTT TCC AAC TTG ACA GCT ACA ACG CAG GGT
GGA TTG GGG ATG GTC GGG CAA AGG TTG AAC TGT CGA TGT TGC GTC CCA
 P   N   P   Y   Q   P   V   S   N   L   T   A   T   T   Q   G 2980          2990          3000          3010          3020
      *             *             *             *             *
CAG AAA GTA ACG CTC AAG TGG GAT GCA CCG AGC ACG AAA ACC AAT GCA
GTC TTT CAT TGC GAG TTC ACC CTA CGT GGC TCG TGC TTT TGG TTA CGT
 Q   K   V   T   L   K   W   D   A   P   S   T   K   T   N   A>

3030          3040          3050          3060          3070
          *             *             *             *             *
ACC ACT AAT ACC GCT CGC AGC GTG GAT GGC ATA CGA GAA TTG GTT CTT
TGG TGA TTA TGG CGA GCG TCG CAC CTA CCG TAT GCT CTT AAC CAA GAA
 T   T   N   T   A   R   S   V   D   G   I   R   E   L   V   L 3080          3090          3100          3110          3120
             *             *             *             *             *
CTG TCA GTC AGC GAT GCC CCC GAA CTT CTT CGC AGC GGT CAG GCC GAG
GAC AGT CAG TCG CTA CGG GGG CTT GAA GAA GCG TCG CCA GTC CGG CTC
 L   S   V   S   D   A   P   E   L   L   R   S   G   Q   A   E
                                             ─── ─── ─── ─── ───

3130          3140          3150
          *             *             *
ATT GTT CTT GAA GCT CAC GAT GTT TGG AAT GAT GGA TCC
TAA CAA GAA CTT CGA GTG CTA CAA ACC TTA CTA CCT AGG
 I   V   L   E   A   H   D   V   W   N   D   G   S>
 ─── ─── ─── ─── ─── ─── ─── ─── ─── ─── ─── ───
```

The nucleotide sequence encoding a mature Arg-gingipain, termed Arg-gingipain-2 herein, extends from 1630–3105. The first ATG appears at nucleotide 949 and is followed by a long open reading frame (ORF) of 2210 nucleotides. This ORF was the largest one observed. However the first ATG is following by 8 others in frame (at nucleotides 1006, 1099, 1192, 1246, 1315, 1321, 1603, and 1609). The most likely candidate to initiate translation is currently unknown. Which of these initiation codons are used in translation of the Arg-gingipain-2 precursor can be determined by expression of the polyprotein in bacteria and subsequent amino-terminal sequence analysis of proprotein intermediates. The sequence derived from 5' noncoding sequences is composed of 948 bp. The primary structure of the mature Arg-gingipain molecule can be inferred from the empirical amino-terminal and carboxy-terminal sequences and molecular mass. Thus, mature Arg-gingipain-2 has an amino terminus starting at nucleotide residue 1630 in SEQ ID NO:4 and at amino acid 1 in SEQ ID NO:5. As expected for an arginine-specific protease, the mature protein is cleaved after an arginine residue. The 50 kDa and the 44 kDa bands from Bz-L-Arg-pNa activity peaks have an identical sequence to that deduced amino acid sequence of gingipain, encoded respectively at nucleotides 1630–1695 and at nucleotides 3106–3156. From these data, the carboxyl terminus is most likely derived from autoproteolytic processing after the arginine residue at 3103–3105 where the amino terminus encoding sequence of hemagglutinin starts (nucleotide 3106). The deduced 492 amino acids of gingipain-2 give rise to a protease molecule with a calculated molecular weight of 54 kDa which correlates well with the molecular mass of 50 kDa determined by SDS-PAGE analysis. Table 5 (see also SEQ ID NO:4) presents the coding sequence and deduced amino acid sequence of gingipain-2. The first nucleotide presented in the sequence belongs to the PstI cloning site and is referred as nucleotide 1. Bold face letters indicate the potential sites of initiation ATG and the first codon of the mature gingipain-2. The amino terminal sequence of gingipain-2 and the amino terminal sequence of 44 kDa bands from Bz-L-Arg-pNa activity peaks are underlined.

A comparison of the deduced amino acid sequence of gingipain-2 with sequences of cysteine proteases indicates some homology around the residues making up the active site (Chua et al. 1988, *J. Exp. Med.* 167, 175–182) (Table 6). The homology between gingipain-2 and cysteine proteases is underlined and is encoded at nucleotide residues 2743 to 2781 in Table 5.

TABLE 6

Composite alignment of the deduced partial amino acid sequence of gingipain-2 with sequences of known cysteine proteases

| Gingipain: | SCDYNGAIATI SA | (SEQ ID NO:11) |
| --- | --- | --- |
| Der p 1: | SCWAFSGVAATFSA | (SEQ ID NO:12) |
| Rat cathepsin H: | SCWIFSTIGALFSA | (SEQ ID NO:13) |
| Chinese gooseberry actinidin: | GCWAFSAIATVEGI | (SEQ ID NO:14) |
| Papaya papain: | SCWAFSAVVTIFGI | (SEQ ID NO:15) |
| Human cathepsin B: | SCWAFGAVEAISDR | (SEQ ID NO:16) |

The first serine residue of Arg-gingipain-2 shown in this table is encoded at nucleotides 2743–2745 of SEQ ID NO:4. SEQ ID NO:4 comprises the exemplified coding sequence for the Arg-gingipain-2 mature protein from *P. gingivalis* strain H66 (see also Table 5). The skilled artisan recognizes that other *P. gingivalis* strains can have coding sequences for a protein with the distinguishing characteristics of an Arg-gingipain; those coding sequences may be identical to or synonymous with the exemplified coding sequence, or there may be some variation(s) in the encoded amino acid sequence. An Arg-gingipain coding sequence from a *P. gingivalis* strain other than H66 can be identified by, e.g. hybridization to a polynucleotide or an oligonucleotide having the whole or a portion of the exemplified coding sequence for mature gingipain, under stringency conditions appropriate to detect a sequence of at least 70% homology.

It is also understood by the skilled artisan that there can be limited numbers of amino acid substitutions in a protein without significantly affecting function, and that nonexemplified gingipain-1 proteins can have some amino acid sequence diversion from the exemplified amino acid sequence. Such naturally occurring variants can be identified, e.g., by hybridization to the exemplified (mature) Arg-gingipain-2 coding sequence under conditions appropriate to detect at least about 70% nucleotide sequence homology, preferably about 80%, more preferably about 90% and most preferably 95–100% sequence homology.

It is well known in the biological arts that certain aminio acid substitutions can be made in protein sequences without affecting the function of the protein. Generally, conservative amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure,* Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

A polynucleotide or fragment thereof is "substantially homologous" (or "substantially similar") to another polynucleotide if, when optimally aligned (with appropriate nucleotide insertions or deletions) with another polynucleotide, there is nucleotide sequence identity for approximately 60% of the nucleotide bases, usually approximately 70%, more usually about 80%, preferably about 90%, and more preferably about 95% to 100% of the nucleotide bases.

Alternatively, substantial homology (or similarity) exists when a polynucleotide or fragment thereof will hybridize to another under polynucleotide under selective hybridization conditions. Selectivity of hybridization exists under hybridization conditions which allow one to distinguish the target polynucleotide of interest from other polynucleotides. Typically, selective hybridization will occur when there is approximately 55% similarity over a stretch of about 14 nucleotides, preferably approximately 65%, more preferably approximately 75%, and most preferably approximately 90%. See Kanehisa (1984) *Nuc. Acids Res.,* 12:203–213. The length of homology comparison, as described, may be over longer stretches, and in certain embodiments will often be over a stretch of about 17 to 20 nucleotides, and preferably about 36 or more nucleotides.

The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C. typically in excess of 37° C., and preferably in excess of 45° C. Stringent salt conditions will ordinarily be less than 1M, typically less than 500 mM, and preferably less than 200mM. However, the combination of parameters is much more important than the measure of any single parameter (Wetmur and Davidson (1968) *J. Mol. Biol.* 31, 349–370).

An "isolated" or "substantially pure" polynucleotide is a polynucleotide which is substantially separated from other polynucleotide sequences which naturally accompany a native gingipain-1 sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to "encode" a polypeptide if, in its native state or when manipulated by methods known to those skilled in the art, it can be transcribed and/or translated to produce the polypeptide of a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term "recombinant" polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other Arg-gingipain coding sequences. Probes comprising synthetic oligonucleotides or other polynucleotides may be derived from naturally occurring or recombinant single or double stranded nucleic acids or be chemically synthesized. Polynucleotide probes may be labelled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a proteinase or a fragment thereof will be incorporated into recombinant polynucleotide constructs, typically DNA constructs, capable of introduction into and replication in a prokaryotic or eukaryotic cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli*, although other prokaryotes, such as *Bacillus subtilis* or Pseudomonas may also be used. Mammalian or other eukaryotic host cells include yeast, filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.*, 22,1859–1862 or the triester method according to Matteuci et al. (1981) *J. Am. Chem. Soc.*, 103, 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1987) *Current Protocols in Molecular Biology*, Greene Publishing and Wiley Interscience, New York; and Metzger et al. (1988) *Nature*, 334,31–36. Many useful vectors for expression in bacteria, yeast, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

The recombinant vectors containing the Arg-gingipain coding sequences of interest can be introduced (transformed, transfected) into the host cell by any of a number of appropriate means, including electroporation; transformation or transfection employing calcium chloride, rubidium chloride, calcium phosphate, DEAE-dextran, or other substances; microprojectile bombardment; lipofection; and transfection or infection (where the vector is an infectious agent, such as a viral or retroviral genome). The choice of such means will often depend on the host cell. Large quantities of the polynucleotides and polypeptides of the present invention may be prepared by transforming suitable prokaryotic or eukaryotic host cells with gingipain-1-encoding polynucleotides of the present invention in compatible vectors or other expression vehicles and culturing such transformed host cells under conditions suitable to attain expression of the Arg-gingipain-encoding gene. The Arg-gingipain may then be recovered from the host cell and purified.

The coding sequence for the "mature" form of Arg-gingipain-2 is expressed after PCR site-directed mutagenesis and cloning into an expression vector suitable for use in *E. coli*, for example. Exemplary expression vectors for *E. coli* and other host cells are given, for example in Sambrook et al. (1989), vide infra, and in Pouwels et al. (Eds.) (1986) *Cloning Vectors*, Elsevier Science Publishers, Amsterdam, the Netherlands.

In order to eliminate leader sequences and precursor sequences at the 5' side of the coding sequence, a combination of restriction endonuclease cutting and site-directed mutagenesis via PCR using an oligonucleotide containing a desired restriction site for cloning (one not present in coding sequence), a ribosome binding site, an translation initiation codon (ATG) and the codons for the first amino acids of the mature Arg-gingipain-2. The oligonucleotide for site-directed mutagenesis at the 3' end of the coding sequence for mature gingipain-1 includes nucleotides encoding the carboxyterminal amino acids of mature gingipain-1, a translation termination codon (TAA, TGA or TAG), and a second suitable restriction endonuclease recognition site not present in the remainder of the DNA sequence to be inserted into the expression vector. The site-directed mutagenesis strategy is similar to that of Boone et al. (1990) *Proc. Natl. Acad. Sci. USA* 87, 2800–2804, as modified for use with PCR.

In another embodiment, polyclonal and/or monoclonal antibodies capable of specifically binding to a proteinase or fragments thereof are provided. The term antibody is used to refer both to a homogenous molecular entity, or a mixture such as a serum product made up of a plurality of different molecular entities. Monoclonal or polyclonal antibodies specifically reacting with the Arg-gingipains may be made by methods known in the art. See, e.g., Harlow and Lane (1988) *Antibodies: A Laboratory Manual,* CSH Laboratories; Goding (1986) *Monoclonal Antibodies: Principles and Practice,* 2d ed., Academic Press, New York; and Ausubel et al. (1987) supra. Also, recombinant immunoglobulins may be produced by methods known in the art, including but not limited to the methods described in U.S. Pat. No. 4,816,567. Monoclonal antibodies with affinities of $10^8 M^{-1}$, preferably $10^9$ to $10^{10}$ or more are preferred.

Antibodies specific for Arg-gingipains may be useful, for example, as probes for screening DNA expression libraries or for detecting the presence of Arg-gingipains in a test sample. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States Patents describing the use of such labels include but are not limited to U.S. Pat. Nos. 3,817,837; 3,850,752; 3,939,350; 3,996,345; 4,277,437; 4,275,149; and 4,366,241.

Antibodies specific for Arg-gingipain(s) and capable of inhibiting its proteinase activity may be useful in treating animals, including man, suffering from periodontal disease. Such antibodies can be obtained by the methods described above and subsequently screening the Arg-gingipain-specific antibodies for their ability to inhibit proteinase activity.

Compositions and vaccine preparations comprising substantially purified Arg-gingipain(s) derived from *P. gingivalis* and a suitable carrier therefor are provided. Such vaccines are useful, for example, in immunizing an animal, including humans, against inflammatory response and tissue damage caused by *P. gingivalis* in periodontal disease. The vaccine preparations comprise an immunogenic amount of one or more Arg-gingipains or an immunogenic fragment(s) or subunit(s) thereof. Such vaccines may comprise one or more Arg-gingipain proteinases, or in combination with another protein or other immunogen. By "immunogenic amount" is meant an amount capable of eliciting the production of antibodies directed against Arg-gingipain(s) in an individual to which the vaccine has been administered.

Immunogenic carriers may be used to enhance the immunogenicity of the proteinases. Such carriers include but are not limited to proteins and polysaccharides, liposomes, and bacterial cells and membranes. Protein carriers may be joined to the proteinases to form fusion proteins by recombinant or synthetic means or by chemical coupling. Useful carriers and means of coupling such carriers to polypeptide antigens are known in the art.

The vaccines may be formulated by any of the means known in the art. Such vaccines are typically prepared as injectables, either as liquid solutions or suspensions. Solid forms suitable for solution in, or suspension in, liquid prior to injection may also be prepared. The preparation may also, for example, be emulsified, or the protein encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3 hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

Arg-gingipain-1 and/or gingipain-2 and fragments of either or both thereof or high molecular weight Arg-gingipain may be formulated into vaccines as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylaminoethanol, histidine, and procaine.

The vaccines are administered in a manner compatible with the dosage formulation, and in such amount as will be prophylactically and/or therapeutically effective. The quantity to be administered, which is generally in the range of about 100 to 1,000 µg of protein per dose, more generally in the range of about 5 to 500 µg of protein per dose, depends on the subject to be treated, the capacity of the individual's immune system to synthesize antibodies, and the degree of protection desired. Precise amounts of the active ingredient required to be administered may depend on the judgment of the physician or doctor of dental medicine and may be peculiar to each individual, but such a determination is within the skill of such a practitioner.

The vaccine may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

A method of monitoring the exposure of an animal or human to Arg-gingipain is provided. Such monitoring methods are useful, for example, in monitoring the progress of a therapy designed to lessen the symptoms of periodontitis.

In general, a biological sample obtained from the animal (e.g., blood, saliva, tissue) is incubated with Arg-gingipain or portions thereof under conditions suitable for antibody-antigen interactions. The detection of the formation of such interactions is indicative of prior exposure of the animal and the subsequent development of an immune response to the proteinase. Examples of such tests include but are not limited to enzyme-linked immunosorbent assays (ELISA).

Alternatively, the subject may be exposed to gingipain-1 and the subsequent reaction monitored. Such exposure may be cutaneously (e.g., by application to the skin via pricking or scratching), intracutaneously (e.g., via intracutaneous injection), subcutaneously, or introduced in the form of an aerosol (generally an aqueous aerosol) into the nasal or bronchial passages (nasoprovocation or bronchoprovocation, respectively), using methods well known in the art. Typical reactions, e.g., a weal and erythema in skin testing, or precipitin reactions measured in vitro, indicate an immunological response to the protein. See, e.g., *Basic and Clinical Immunology*, 6th ed., Stites et al., eds., (Appleton & Lange, 1987), pp. 436–438, for a general description.

An Arg-gingipain may also be used in methods of identifying agents that modulate proteinase activity, e.g., by acting on the proteinase itself. One such method comprises the steps of incubating Arg-gingipain-1 (or high molecular weight Arg-proteinase) with a putative therapeutic agent; determining the activity of the proteinase incubated with the agent; and comparing the activity obtained in step with the activity of a control sample of proteinase that has not been incubated with the agent.

All references cited herein are hereby incorporated by reference in their entirety.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) Meth. Enzymol. 218, Part I; Wu (ed.) (1979) Meth Enzymol. 68; Wu et al. (eds.) (1983) Meth. Enzymol. 100 and 101; Grossman and Moldave (eds.) Meth. Enzymol. 65; Miller (ed.) (1972) *Experiments in Molecular Genetics*, Cold spring Harbor Laboratory, Cold Spring Harbor, N.Y., Old Primrose (1981) *Principles of Gene Manipulation*, University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

The foregoing discussion and the following examples illustrate but are not intended to limit the invention. The skilled artisan will understand that alternative methods may be used to implement the invention.

EXAMPLE 1 PURIFICATION OF GINGIPAIN ENZYMES

Example 1.1

Bacterial Cultivation

*P. gingivalis* strain H66 was obtained from Roland Arnold (Emory University, Atlanta, Ga.). Cells were grown in 500 ml of broth containing 15.0 g Trypticase Soy Broth (Difco, Detroit, Mich.), 2.5 g yeast extract, 2.5 mg hemin, 0.25 g cysteine, 0.05 g dithiothreitol, 0.5 mg menadione (all from Sigma Chemical Company, St. Louis, Mo.) anaerobically at 37° C. for 48 hr in an atmosphere of 85% $N_2$, 10% $CO_2$, 5% $H_2$. The entire 500 ml culture was used to inoculate 20 liters of the same medium, and the latter was incubated in a fermentation tank at 37° C. for 48 hr (to a final optical density of 1.8 at 650 nm).

Example 1.2

Proteinase Purification (Low Molecular Weight Arg-gingipain)

1200 ml cell-free supernatant was obtained from the 48 hr culture by centrifugation at 18,000×g for 30 min. at 4° C. Proteins in the supernatant were precipitated out by 90% saturation with ammonium sulfate. After 2 hr at 4° C., the suspension was centrifuged at 18,000×g for 30 min. The resulting pellet was dissolved in 0.05M sodium acetate buffer, pH 4.5, 0.15 NaCl, 5 mM $CaCl_2$; the solution was dialyzed against the same buffer overnight at 4° C., with three changes with a buffer:protein solution larger than 150:1. The dialysate was then centrifuged at 25,000×g for 30 min., and the dark brown supernatant (26 ml) was then chromatographed over an agarose gel filtration column (5.0×150 cm; Sephadex G-150, Pharmacia, Piscataway, N.J.) which had been pre-equilibrated with the same buffer. The column was developed with said buffer at a flow rate of 36 ml/hr. 6 ml fractions were collected and assayed for both amidolytic and proteolytic activities, using Bz-L-Arg-pNA and azocasein as substrates. Four peaks containing amidolytic activity were identified (FIG. 1). The fractions corresponding to peak 4 were combined, concentrated by ultrafiltration (Amicon PM-10 membrane; Amicon, Beverly, Mass.) and then dialyzed overnight against 0.05 Bis-Tris, 5 mM $CaCl_2$, pH 6.0. The volume of the dialysate was 14 ml.

The 14 ml dialysate from the previous step was then applied to a DEAE-cellulose (Whatman, Maidstone, England) column (1×10 cm) equilibrated with 0.05 mM Bis-Tris, 5 mM $CaCl_2$, pH 6.0. The column was then washed with an additional 100 ml of the same buffer. About 75% of the amidolytic activity, but only about 50% of the protein, passed through the column. The column wash fluid was dialyzed against 0.05M sodium acetate buffer containing 5 mM $CaCl_2$ (pH 4.5). This 19 ml dialysate was applied to a Mono S FPLC column (Pharmacia LKB Biotechnology Inc., Piscataway, N.J.) equilibrated with the same buffer. The column was washed with the starting buffer at a flow rate of 1.0 ml/min for 20 min. Bound proteins were eluted first with a linear NaCl gradient (0 to 0.1M) followed by a second linear NaCl gradient (0.1 to 0.25 M), each gradient applied over a 25 min time period. Fractions were assayed for amidolytic activity using Bz-L-Arg-pNA. Fractions with activity were pooled and re-chromatographed using the same conditions. Although not detectable by gel electrophoresis, trace contamination by a proteinase capable of cleaving after lysyl residues was sometimes observed. This contaminating activity was readily removed by applying the sample to an arginyl-agarose column (L-Arginyl-SEPHAROSE 4B) equilibrated with 0.025M Tris-HCl, 5 mM $CaCl_2$, 0.15M NaCl, pH 7.5. After washing with the same buffer, purified enzyme was eluted with 0.05M sodium acetate buffer, 5 mM $CaCl_2$, pH 4.5. Yields of gingipain-1 were markedly reduced by this step (about 60%).

Example 1.3

Proteinase Purification (High Molecule Weight Gingipain)

The culture supernatant (2,900 ml) was obtained by centrifugation of the whole culture (6,000×g, 30 min, 4° C.). Chilled acetone (4,350 ml) was added to this fraction over a period of 15 min, with the temperature of the solution maintained below 0° C. at all times, using an ice/salt bath and this mixture was centrifuged (6,000×g, 30 min, −15° C.). The precipitate was dissolved in 290 ml of 20 mM Bis-Tris-HCl, 150 mM NaCl, 5 mM $CaCl_2$, 0.02% (w/v) $NAN_3$, pH 6.8 (Buffer A), and dialyzed against Buffer A containing 1.5 mM 4,4'-Dithiodipyridine disulphide for 4 h, followed by 2 changes of buffer A overnight. The dialyzed fraction was centrifuged (27,000×g, 30 min, 4° C.), following which it was concentrated to 40 ml by ultrafiltration using an Amicon PM-10 membrane. This concentrated fraction was applied to a Sephadex G-150 column (5×115 cm=2260 ml; Pharmacia, Piscataway, N.J.) which had previously been equilibrated with Buffer A, and the fractionation was carried out at 30 ml/h (1.5 cm/h). Fractions (9 ml) were assayed for activity against Bz-L-Arg-pNa and Z-L-Lys-pNa (Novabiochem; 0.5 mM). Amidolytic activities for Bz-L-Arg-pNa (0.5mM) or Z-L-Lys-pNa were measured in 0.2M Tris.Hcl, 1 mM $CaCl_2$, 0.02% (w/v) $NaN_3$, 10 mM L-cysteine, pH 7.6. General proteolytic activity was measured with azocasein (2% w/v) as described by Barrett and Kirschke (1981) *Meth. Enzymol.* 80, 535–561 for cathepsin L. Three peaks with activity against the two substrates were found. The first (highest molecular weight) peak of activity was pooled, concentrated to 60 ml using ultrafiltration and dialyzed overnight against two changes of 50 mM Tris-HCl, 1 mM $CaCl_2$, 0.02% $NaN_3$, pH 7.4 (Buffer B).

This high MW fraction was applied to an L-Arginine-Sepharose column (1.5×30 cm=50 ml), which had previously been equilibrated with Buffer B at a flow rate of 20 ml/hr (11.3 cm/h), following which the column was washed with two column volumes of Buffer B. Following this, a step gradient of 500 mM NaCl was applied in Buffer B and the column was washed with this concentration of NaCl until the A280 baseline fell to zero. After re-equilibration of the column in Buffer B, a gradient from 0–750 mM L-Lysine was applied in a total volume of 300 ml, followed by 100 ml of 750 mM L-Lysine. The column was once again re-equilibrated with Buffer B and a further gradient to 100 mM L-arginine in 300 ml was applied in the same way. Fractions (6 ml) from the Arg wash were assayed for activity against the two substrates as described previously. The arginine gradient eluted a major peak for an enzyme degrading Bz-L-Arg-pNa. The active fractions were pooled and dialyzed against two changes of 20 mM Bis-Tris-HCl, 1 mM $CaCl_2$, 0.02% (v/w) $NaN_3$, pH 6.4 (Buffer C) and concentrated down to 10 ml using an Amicon PM-10 membrane.

The concentrate with activity for cleaving Bz-L-Arg-pNa was applied to a Mono Q FPLC column (Pharmacia LKB Biotechnology Inc, Piscataway, N.J.) equilibrated in Buffer C, the column was washed with 5 column volumes of Buffer C at 1.0 ml/min, following which bound protein was eluted with a 3 step gradient [0–200 mM NaCl (10 min), followed by 200–250 mM NaCl (15 min) and 250–500 mM NaCl (5 min)]. The active fractions from Mono Q were pooled and used for further analyses.

EXAMPLE 2 CHARACTERIZATION OF GINGIPAIN-1

Example 2.1

Molecular Weight Determination

The molecular weight of the purified Arg-gingipain-1 was estimated by gel filtration on a Superose 12 column (Pharmacia, Piscataway, N.J.) and by Tricine-SDS polyacrylamide gel electrophoresis. In the latter case, 1 mM TLCK was used to inactivate the protease prior to boiling, thus preventing autoproteolytic digestion.

Example 2.2

Enzyme Assays

Amidolytic activities of *P. gingivalis* proteinases were measured with the substrates MeO-Suc-Ala-Ala-Pro-Val-pNA at a concentration of 0.5 mM, Suc-Ala-Ala-Ala-pNA (0.5 mM), Suc-Ala-Ala-Pro-Phe-pNA (0.5 mM), Bz-Arg-pNA (1.0 mM), Cbz-Phe-Leu-Glu-pNA) (0.2 mM); S-2238, S-2222, S-2288 and S-2251 each at a concentration of 0.05 mM; in 1.0 ml of 0.2M Tris-HCl, 5 mM $CaCl_2$, pH 7.5. In some cases either 5mM cysteine and/or 50 mM glycylglycine (Gly-Gly) was also added to the reaction mixture.

For routine assays, pH optimum determination and measurement of the effect of stimulating agents and inhibitors on trypsin-like enzymes, only Bz-L-Arg-pNA was used as substrate. Potential inhibitory or stimulatory compounds were preincubated with enzyme for up to 20 min at room temperature at pH 7.5, in the presence of 5 mM $CaCl_2$ (except when testing the effects of chelating agents) prior to the assay for enzyme activity.

General proteolytic activity was assayed using the same buffer system as described for detecting amidolytic activity, but using azocoll or azocasein (1% w/v) as substrate.

A unit of Arg-gingipain-1 enzymatic activity is based on the spectroscopic assay using benzoyl-Arg-p-nitroanilide as substrate and recording Δ absorbance units at 405 nm/min/absorbance unit at 280 nm according to the method of Chen et al. (1992) Supra.

Example 2.3

Enzyme Specificity

Purified Arg-gingipain-1 (0.8 µg) in 50 mM ammonium bicarbonate buffer, pH 7.7, 5 mM $CaCl_2$, was preincubated with 2 mM cysteine for 10 min, followed by the addition of either oxidized insulin B chain (225 µg) or melittin (225 µg) at 25° C. Samples were removed after various time intervals, and the reaction mixtures were subjected to HPLC (reverse phase column, MicroPak SP C-18 column) using linear gradients (0.08% trifluoroacetic acid to 0.08% trifluoroacetic acid plus 80% acetonitrile, over a 45 min period (flow rate 1.0 ml/min). Peptides were detected by monitoring $A_{220}$. Product peaks were collected and subjected to amino acid analysis and/or amino-terminal sequence analysis.

Example 2.4

Amino Acid Sequence Analysis

Amino-terminal amino acid sequence analysis of either Arg-gingipain-1 or degradation products from proteolytic reactions was carried out using an Applied Biosystems 4760A gas-phase sequenator, using the program designed by the manufacturer.

The amino acid sequence of the COOH terminus of SDS-denatured Arg-gingipain-1 and of Arg-gingipain-2 was determined. 10 nmol aliquots of gingipain-1 were digested in 0.2M N-ethylmorpholine acetate buffer, pH 8.0, with carboxypeptidase A and B at room temperature, using 1:100 and 1:50 molar ratios, respectively. Samples were removed at intervals spanning 0 to 12 hours, boiled to inactivate the carboxypeptidase, and protein was precipitated with 20% tricholoracetic acid. Amino acid analysis was performed on the supernatants.

Example 2.5

Materials

MeO-Suc-Ala-Ala-Pro-Val-pNA, Suc-Ala-Ala-Pro-Phe-pNA, Gly-Pro-pNA, Suc-Ala-Ala-Ala-pNA, Bz-Arg-pNA, diisopropylfluorophosphate, phenylmethylsulfonyl fluoride, tosyl-L-lysine chloromethyl ketone (TLCK), tosyl-L-phenylalanine chloromethyl ketone (TPCK), trans-epoxysuccinyl-L-leucylamide-(4-guanidino)butane), an inhibitor of cysteine proteinases, leupeptin, antipain and azocasein were obtained from Sigma Chemical Co., St. Louis, Mo. 3,4-Dichloroisocoumarin was obtained from Boehringer, Indianapolis, Ind. and CBz-Phe-Leu-Glu-pNA and azocoll were obtained from Calbiochem, La Jolla, Calif. S-2238 (D-Phe-Pip-Arg-pNA), S-2222 (Bz-Ile-Glu-(γ-OR)-Gly-Arg-pNA), S-2288 (D-Ile-Pro-Arg-pNA), and S-2251 (D-Val-Leu-Lys-pNA) were from Kabi-Vitrum, (Beaumont, Tex.).

EXAMPLE 3 COMPLEMENT ACTIVATION BY ARG-GINGIPAIN-1

Example 3.1 cPreparation of C3 and C5

Human complement protein C3 was isolated according to the procedures described by Tack and Prahl (1976) Biochemistry 15, 4513–4521, and C5 was isolated by the method of DeScipio, R. G. (1981) Biochem J. 199, 485–496 as modified by Parkes et al. (1981) Biochem J. 193, 963–970. Outdated human plasma treated with barium citrate, and C3 and C5 were precipitated with 4–12% polyethylene glycol. The preparation was then fractionated over DEAE-Sephadex and by gel filtration through Sephacryl S-300. The C3, C3u, and C5 were separated using sulfated Sepharose. Contaminating C3u was removed from C5 by passage through a column of rabbit anti-C3 IgG-Sepharose. The C3 and C5 were further purified to apparent homogeneity, as visualized by SDS-PAGE, by FPLC using a Mono Q (5×55 mm) anion-exchange column (Pharmacia LKB Biotechnology Inc.).

Human C5a and C3a were prepared according to the methods described by Hugli and co-workers [Hugli et al. (1975) J. Biol. Chem. 250, 1472–1478; Fernandez and Hugli (1976) J. Immunol. 117, 1688–1694; Hugli et al. (1981) Mol. Cell. Biochem. 41, 59–66].

Example 3.2

Gingipain-1 Digests of C3 and C5

Human C3 or C5 was incubated with purified Arg-gingipain-1 (purification included affinity chromatography over L-Arginyl-Sepharose 4B as described in Example 1.2) with a molar ratio of substrate to enzyme of 25:1 for an Arg-gingipain-1 preparation having a specific activity of 728 units or with a molar ratio of 100:1 for a gingipain-1 preparation having a specific activity of 1123 units. Incubations were carried out in 10 mM Tris HCl, 1 mM cysteine, 5 mM $CaCl_2$, and with or without 50 mM glycyl-glycine at pH 7.0 and 37° C. This incubation mixture, exclusive of the glycyl-glycine, will be referred to as the digestion buffer. At designated time points aliquots were removed, and proteolysis was inhibited by adding TLCK to a final concentration of 2 mM.

Example 3.3

Sequence Analysis of C5 Fragments

Amino acid sequence analyses of the α-chain fragments of C5 cleaved by Arg-gingipain-1 were obtained after SDS-PAGE separation. The fragments were blotted onto Immobilon transfer membranes (Millipore Corp., Bedford, Mass.). Eight to 10 cycles of automated Edman degradation [Edman and Begg (1967) Eur. J. Biochem. 1, 80–91] were performed using an Applied Biosystems 470A Protein Sequencer. The amino termini of C5 fragments were assigned based on the known primary structure of C5 [Haviland, et al. (1991) J. Immunol 146, 362–368].

Example 3.4

Electrophoresis

SDS-PAGE of Arg-gingipain-1 was performed as in Laemmli (1970) Nature 227: 680–685. Prior to electrophoresis the samples were boiled in a buffer containing 20% glycerol, 4% SDS, and 0.1% bromphenol blue. The samples were run under reducing conditions by adding 2% β-mercaptoethanol unless otherwise noted. Samples were heated for 5 min at 100° C. prior to loading onto gels. A 5–15% gradient gel was used for the initial digests of C3 and C5, and the gels were subsequently stained with Coomassie Brilliant Blue R. The C5 digest used to visualize breakdown products before and after reduction of the disulfide bonds were electrophoresed in a 8% gel. Attempts to visualize C5a in the C5 digest were carried out using 13% gels that were developed with silver stain according to the method of Merril et al. (1979) Proc. Natl. Acad. Sci USA 76, 4335–4340.

In some experiments (high molecular weight forms) SDS-PAGE using Tris-HCl/tricine buffer was carried out per Shagger and Van Jagow (1987) Analyt. Biochem. 166, 368–379.

Electrophoresis on cellulose acetate strips were performed in 0.075 barbital buffer at pH 8.5 and 4° C. for 30 min. at 200 V. The Beckman Microzone apparatus (model R101) used for the electrophoresis of the protein, and the strips were stained using Amido Black.

Example 3.5

Neutrophil Isolation

Neutrophils (polymorphonuclear leukocytes, PMNs) were isolated from peripheral blood of healthy human donors according to the method described by Fehr and Dahinden (1979) J. Clin. Invest. 64, 8–16. Blood was drawn into syringes containing a final concentration of 10 mM EDTA. Blood was mixed in a 50-ml conical tube containing an equal volume of sterile, nonpyrogenic 6% dextran and 0.9% saline (Baxter). Cells were allowed to sediment for 60 min. at room temperature. The leukocyte-rich upper layer was collected, and 30 ml was carefully layered over 15 ml of Ficoll-Paque (Pharmacia) and centrifuged for 25 min. at 300×g in a Sorvall RT6000B centrifuge. The pellet containing PMNs was depleted of red blood cells by hypotonic lysis. The PMNs were then washed twice in Earle's balanced salt solution (EBSS, Gibco, Grand Island, N.Y.) containing 10 mM MOPS/HCl at pH 7.3. The PMNs to be used in the polarization assay were in EBSS and MOPS/HCl, and cells used for the chemotaxis assay were resuspended in EBSS containing 1% bovine serum albumin (Sigma).

Example 3.6

Polarization Assay

The effect of products in the C5 digest on the morphology of PMNs was measured according to the assay described by Haston and Shields (1985) *J. Immunol. Methods* 81, 229–237. The C5 (90 µg) was incubated with Arg-gingipain-1 (25:1; molar ratio of C5 to enzyme) in 200 µl of digestion buffer for 180 min. at 37° C. Controls devoid of either enzyme or C5 were incubated under identical conditions. PMNs (4×10⁶/ml) were incubated with aliquots of the C5 digest for 30 min at 37° C., then fixed with 2.5% ice-cold glutaraldehyde (2.5% glutaraldehyde in 0.9% saline, Fisher) for 2 h at 4° C. Cells were examined microscopically, and cells that deviated from the typical spherical shape were scored as polarized. The results are expressed as a percent of cells polarized (200 cells were counted per sample).

Example 3.7

Chemotaxis Assay

Chemotaxis of PMNs was measured as described by Dahinden et al. (1983) *J. Immunol.* 130, 857–862, in modified Boyden chambers (Adaps, Inc., Dedham, Mass., models P1 and 1/2SC). The C5 was incubated with gingipain-1 at a 100:1 molar ratio in digestion buffer for 90 min at 37° C. Controls were run as above.

Cells that migrated through the entire thickness of an 8-µm micropore filter (Sartorius, Gottingen, Federal Germany of Germany) were counted after 90 min. in an incubator (5% $CO_2$) at 37° C. The upper chamber contained the purified PMNs (3×10⁶/ml), and the lower chamber contained the chemoattractant in EBSS/albumin buffer. Zymosan-activated serum was used at 1:5 dilution as the reference chemoattractant. Results were expressed as a percentage of the 1:5 diluted zymosan-activated serum control. The buffer control typically gave 2% of the zymosan-activated serum cell response. The number of cells migrating to the lower chamber was determined by a Sysmex F-300 hematology analyzer (TOA Medical Electronics, Kobe, Japan).

Example 3.8

Isolation of C5a-like Peptide

C5 (400 µg) was incubated with Arg-gingipain-1 (100:1 molar ratio) in digestion buffer under the conditions described above. Approximately 2×10⁵ cpm of $^{125}$I-labeled C5 was included in the digestion mixture. C5a labeled with $^{125}$I (5×10⁵ cpm) was added to the digest immediately before it was applied to a P-60 column (1.5×55 cm, Bio-Rad) equilibrated with 20 mM imidazole-HCl, containing 0.3M NaCl, at pH 7.0. The gel filtration was performed at 4° C. using a flow rate of 10 ml/h. Fractions containing radiolabeled C5a were pooled and dialyzed extensively against distilled water at 4° C. This sample was lyophilized to dryness and resuspended in a 4-µl volume of water for analysis.

Example 4.1

Oligonucleotide Synthesis

Oligonucleotide primers for PCR probes and sequencing were synthesized by the phosphoraminite method with an Applied Biosystems model 394 automated DNA synthesizer (Applied Bisystems, Foster City, Calif.) and purified by PAGE and desalted on Sep-Pak (Millipore Corp., Beverly, Mass.) using standard protocols. Primer GIN-1-32 was designed to bind to the noncoding strand of Arg-gingipain DNA corresponding to the $NH_2$-terminal portion of the mature protein, i.e., to the sequence encoding amino acids 2–8 within SEQ ID NO:1. The sequence of the 32-base primer consists of 20 bases specific for Arg-gingipain and six additional bases at the 5' end (underlined), as follows: 5'-GGCTTTACNCCNGTNGARGARYTNGA-3' (SEQ ID NO:7), where N is A or G or C or T. Primer GIN-2-30 was designed to bind to the coding strand of Arg-gingipain DNA corresponding to the amino acids 25–32 of the mature protein, i.e., residues 25–32 of SEQ ID NO:1. The sequence of the 30-base primer consists of 24 bases specific for gingipain-1 (and gingipain-2) DNA and six additional bases at the 5' end (underlined), as follows: 5'-GGCTTTRTTYTTCCARTC NACRAARTCYTT-3', where R is A or G, Y is C or T and N is A or G or C or T (SEQ ID NO:8). Primer GIN-8S-48: 5'-CCTGGAGAATTCTCG TATGATCGTCATCGTAGCCAAAAAGTATGAGGG-3' (SEQ ID NO:9) was designed to bind to the noncoding strand of Arg-gingipain DNA corresponding to the amino acids 11–22 of the mature protein, i.e., amino acids 11–22 of SEQ ID NO:1, and was designed on the basis of partial DNA sequence information for the Arg-gingipain coding sequence (nucleotides 1659–1694 of SEQ ID NO:4) and included a 6-base EcoRI restriction site plus six additional bases at the 5' end (underlined). This primer was used as a probe to screen a λDASH *P. gingivalis* genomic DNA library (see below). One additional oligonucleotide GIN-14-20 (20-mers), initially designed to sequence Arg-gingipain DNA, was used as a probe to identify and then clone the 3' end of the gingipain-1 coding sequence. Primer GIN-14-20 was designed to bind to the noncoding strand of gingipain-1 DNA corresponding to 20 bases specific for 3' end of Arg-gingipain (nucleotides 2911–2930 within SEQ ID NO:4): 5'-ATCAACACTAATGGTGAGCC-3' (SEQ ID NO:10). A total of 23 20-mers internal primers were designed to sequence the Arg-gingipain-2 coding sequence using empirically determined sequence.

Example 4.2

Polymerase Chain Reaction

The DNA templates used in PCR was *P. gingivalis* total cellular DNA. The PCR was run using primer GIN-1-32 (SEQ ID NO:7) along with primer GIN-2-30 (SEQ ID NO:8); PCR consistently yielded a single 105-base pair product (P105) detected on a 7% acrylamide gel representing a partial gingipain DNA. After treatment with the Klenow enzyme, P105 was cloned in pCR-Script™SK(+) (Stratagene La Jolla, Calif.). After sequence analysis of P105, specific primer GIN-8S-48 (SEQ ID NO:9) was designed to use as a probe. The $^{32}$P-labeled GIN-8S-48 probe, was generated by kinase reaction for use in subsequent hybridization screening of the λDASH library. Incorporated nucleotides were separated from unincorporated nucleotides on a Sephadex G-25 column (Boehringer Mannheim Corporation, Indianapolis, Ind.)

Example 4.3

Construction of the Genomic DNA Library

A λDASH DNA library was constructed according to the protocols of Stratagene, using the lambda DASH™ II/BamHI cloning kit. A library of 2×10⁵ independent recombinant clones was obtained.

Example 4.4

Screening the cDNA Library

Approximately 2×10⁵ phages were grown on 5×150 mm agar plates, lifted in duplicate onto supported nitrocellulose transfer membrane (BAS-NC, Schleicher & Schuel, Keene, N.H.), hybridized to the ³²P-labeled GIN-8S-48 probe described above. Hybridizations were performed overnight at 42° C. in 2× Denhardt's solution (Denhardt, D. T. (1966), *Biochem. Biophys. Res. Comm.* 23, 641–646), 6× SSC (SSC is 15mM sodium citrate, 150mM NaCl), 0.4% SDS (w/v), 500 µg/ml fish sperm DNA. The filters were washed in 2× SSC containing 0.05% SDS (w/v) at 48° C. Seven positively hybridizing plaques were purified. After extraction and purification, the DNA was analyzed by restriction enzyme digestion and agarose gel electrophoresis. The 3 kb-PstI fragment from clone A1 was subsequently cloned into pBluescript SK(–) (Stratagene, La Jolla, Calif.) and M13mp18 and 19 and sequenced. After restriction analysis of the A1 clone, a SmaI/BamHI fragment was then cloned into pBluescript SK(–). A PstI/BamHI smaller fragment was subcloned into M13mp18 and 19 for sequencing purposes. Standard protocols for cDNA library screening, lambda phage purification, agarose gel electrophoresis and plasmid cloning were employed (Maniatis et al., 1982 supra).

Example 4.5

Southern Blot Analysis

The membranes were washed as described above. BamHI, HindIII- or PstI-digested *P. gingivalis* DNA samples were hybridized with ³²P-labeled GIN-8S-48. Two BamHI fragments of approximately 9.4 and 3.5 kb and two PstI fragments of approximately 9.4 and 3 kb were found. No HindIII fragment was seen. BamHI- and PstI-digested λDASH DNA after purification of positive recombinant clones from the library revealed one clone (A1) with a 3.5 kb BamHI fragment and a 3 kb PstI fragment; One clone (B1) with a 9.4 kb BamHI fragment and a 9.4 kb PstI fragment; And 5 clones with a 9.4 kb BamHI fragment and a 10 kb PstI fragment. The A1 clone was sequenced because the DNA predicted to encode a 50-KDa protein is approximately 1.35 kb. In order to clone the stop codon of Arg-gingipain-2, double PstI/HindIII-digested *P. gingivalis* DNA were hybridized with ³²P-labeled GIN-14-20. One PstI/HindIII fragment of approximately 4.3 kb was found. This fragment was gel purified and cloned into pbluescript SK(–). A smaller fragment (PstI/Asp713) was subcloned into M13mp18 and 19 for sequencing purposes.

Example 4.6

DNA Sequencing

Double-stranded DNA cloned into pBluescript SK(–) and single-stranded DNA cloned into M13mp18 and 19 were sequenced by the dideoxy terminator method [Sanger et al. (1977) *Proc. Natl. Acad. Sci. USA* 74, 5463–5467] using sequencing kits purchased from United States Biochemicals (Sequenase version 2.0). The DNA was sequenced using M13 universal primer, reverse sequencing primer and internal primers according to the strategy presented in FIG. 9.

---

We claim:

1. A recombinant DNA molecule comprising a nucleotide sequence encoding an Arg-gingipain protein having an amino acid sequence as given in SEQ ID NO:5 from amino acid 1 through amino acid 510.

2. The recombinant DNA molecule of claim 1, wherein said nucleotide sequence is as given in SEQ ID NO:4 from nucleotide 1630 through 3105.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
      ( A ) ORGANISM: Porphyromonas gingivalis
      ( B ) STRAIN: H66

( x i ) SEQUENCE DESCRIPTION: SEQ ID NO:1:

```
Tyr  Thr  Pro  Val  Glu  Glu  Lys  Gln  Asn  Gly  Arg  Met  Ile  Val  Ile  Val
 1              5                        10                       15

Ala  Lys  Lys  Tyr  Glu  Gly  Asp  Ile  Lys  Asp  Phe  Val  Asp  Trp  Lys  Asn
               20                        25                       30

Gln  Arg  Gly  Leu  Thr  Lys  Xaa  Val  Lys  Xaa  Ala
          35                        40
```

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

```
Gly  Tyr  Gly  Asp  Ser  Asn  Tyr  Lys
1                   5
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

```
Thr  Leu  Gln  Lys  Lys  Ile  Glu  Glu  Ile  Ala
1                   5                        10
```

( 2 ) INFORMATION FOR SEQ ID NO:4:

( i ) SEQUENCE CHARACTERISTICS:
        ( A ) LENGTH: 3159 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 949..3159

( i x ) FEATURE:
        ( A ) NAME/KEY: mat_peptide
        ( B ) LOCATION: 1630..3105

( x i ) SEQUENCE DESCRIPTION: SEQ ID NO:4:

```
CTGCAGAGGG  CTGGTAAAGA  CCGCCTCGGG  ATCGAGGCCT  TTGAGACGGG  CACAAGCCGC      60
CGCAGCCTCC  TCTTCGAAGG  TGTCTCGAAC  GTCCACATCG  GTGAATCCGT  AGCAGTGCTC     120
ATTGCCATTG  AGCAGCACCG  AGGTGTGGCG  CATCAGATAT  ATTTTCATCA  GTGGATTATT     180
AGGGTATCGG  TCAGAAAAAG  CCTTCCGAAT  CCGACAAAGA  TAGTAGAAAG  AGAGTGCATC     240
TGAAAACAGA  TCATTCGAGG  ATTATCGATC  AACTGAAAAG  GCAGGAGTTG  TTTTGCGTTT     300
```

```
TGGTTCGGAA AATTACCTGA TCAGCATTCG TAAAAACGTG GCGCGAGAAT TTTTTCGTTT    360

TGGCGCGAGA ATTAAAAATT TTTGGAACCA CAGCGAAAAA AATCTCGCGC CGTTTTCTCA    420

GGATTTACAG ACCACAATCC GAGCATTTTC GGTTCGTAAT TCATCGAAGA GACAGGTTTT    480

ACCGCATTGA ATCAGAGAG AGAATATCCG TAGTCCAACG GTTCATCCTT ATATCAGAGG     540

TTAAAAGATA TGGTACGCTC ATCGAGGAGC TGATTGGCTT AGTAGGTGAG ACTTTCTTAA    600

GAGACTATCG GCACCTACAG GAAGTTCATG GCACACAAGG CAAAGGAGGC AATCTTCGCA    660

GACCGGACTC ATATCAAAAG GATGAAACGA CTTTCCATA CGACAACCAA ATAGCCGTCT     720

ACGGTAGACG AATGCAAACC CAATATGAGG CCATCAATCA ATCCGAATGA CAGCTTTTGG    780

GCAATATATT ATGCATATTT TGATTCGCGT TAAAGGAAA AGTGCATATA TTTGCGATTG     840

TGGTATTTCT TTCGGTTTCT ATGTGAATTT TGTCTCCCAA GAAGACTTTA TAATGCATAA    900

ATACAGAAGG GGTACTACAC AGTAAAATCA TATTCTAATT TCATCAAA ATG AAA AAC    957
                                                     Met Lys Asn
                                                     -227     -225
```

```
TTG AAC AAG TTT GTT TCG ATT GCT CTT TGC TCT TCC TTA TTA GGA GGA              1005
Leu Asn Lys Phe Val Ser Ile Ala Leu Cys Ser Ser Leu Leu Gly Gly
        -220                -215                    -210

ATG GCA TTT GCG CAG CAG ACA GAG TTG GGA CGC AAT CCG AAT GTC AGA              1053
Met Ala Phe Ala Gln Gln Thr Glu Leu Gly Arg Asn Pro Asn Val Arg
        -205                -200                    -195

TTG CTC GAA TCC ACT CAG CAA TCG GTG ACA AAG GTT CAG TTC CGT ATG              1101
Leu Leu Glu Ser Thr Gln Gln Ser Val Thr Lys Val Gln Phe Arg Met
        -190                -185                    -180

GAC AAC CTC AAG TTC ACC GAA GTT CAA ACC CCT AAG GGA ATC GGA CAA              1149
Asp Asn Leu Lys Phe Thr Glu Val Gln Thr Pro Lys Gly Ile Gly Gln
        -175                -170                    -165

GTG CCG ACC TAT ACA GAA GGG GTT AAT CTT TCC GAA AAA GGG ATG CCT              1197
Val Pro Thr Tyr Thr Glu Gly Val Asn Leu Ser Glu Lys Gly Met Pro
-160                -155                    -150                    -145

ACG CTT CCC ATT CTA TCA CGC TCT TTG GCG GTT TCA GAC ACT CGT GAG              1245
Thr Leu Pro Ile Leu Ser Arg Ser Leu Ala Val Ser Asp Thr Arg Glu
                    -140                -135                    -130

ATG AAG GTA GAG GTT GTT TCC TCA AAG TTC ATC GAA AAG AAA AAT GTC              1293
Met Lys Val Glu Val Val Ser Ser Lys Phe Ile Glu Lys Lys Asn Val
        -125                -120                    -115

CTG ATT GCA CCC TCC AAG GGC ATG ATT ATG CGT AAC GAA GAT CCG AAA              1341
Leu Ile Ala Pro Ser Lys Gly Met Ile Met Arg Asn Glu Asp Pro Lys
        -110                -105                    -100

AAG ATC CCT TAC GTT TAT GGA AAG AGC TAC TCG CAA AAC AAA TTC TTC              1389
Lys Ile Pro Tyr Val Tyr Gly Lys Ser Tyr Ser Gln Asn Lys Phe Phe
-95                  -90                     -85

CCG GGA GAG ATC GCC ACG CTT GAT GAT CCT TTT ATC CTT CGT GAT GTG              1437
Pro Gly Glu Ile Ala Thr Leu Asp Asp Pro Phe Ile Leu Arg Asp Val
-80                  -75                     -70                  -65

CGT GGA CAG GTT GTA AAC TTT GCG CCT TTG CAG TAT AAC CCT GTG ACA              1485
Arg Gly Gln Val Val Asn Phe Ala Pro Leu Gln Tyr Asn Pro Val Thr
             -60                    -55                    -50

AAG ACG TTG CGC ATC TAT ACG GAA ATC ACT GTG GCA GTG AGC GAA ACT              1533
Lys Thr Leu Arg Ile Tyr Thr Glu Ile Thr Val Ala Val Ser Glu Thr
             -45                    -40                    -35

TCG GAA CAA GGC AAA AAT ATT CTG AAC AAG AAA GGT ACA TTT GCC GGC              1581
Ser Glu Gln Gly Lys Asn Ile Leu Asn Lys Lys Gly Thr Phe Ala Gly
        -30                  -25                     -20

TTT GAA GAC ACA TAC AAG CGC ATG TTC ATG AAC TAC GAG CCG GGG CGT              1629
Phe Glu Asp Thr Tyr Lys Arg Met Phe Met Asn Tyr Glu Pro Gly Arg
        -15                  -10                     -5
```

| | | | | | | | | | | | | | | | | |
|---|---|---|---|---|---|---|---|---|---|---|---|---|---|---|---|---|
| TAC | ACA | CCG | GTA | GAG | GAA | AAA | CAA | AAT | GGT | CGT | ATG | ATC | GTC | ATC | GTA | 1677 |
| Tyr | Thr | Pro | Val | Glu | Glu | Lys | Gln | Asn | Gly | Arg | Met | Ile | Val | Ile | Val | |
| 1 | | | | 5 | | | | | 10 | | | | | 15 | | |
| GCC | AAA | AAG | TAT | GAG | GGA | GAT | ATT | AAA | GAT | TTC | GTT | GAT | TGG | AAA | AAC | 1725 |
| Ala | Lys | Lys | Tyr | Glu | Gly | Asp | Ile | Lys | Asp | Phe | Val | Asp | Trp | Lys | Asn | |
| | | | 20 | | | | | 25 | | | | | 30 | | | |
| CAA | CGC | GGT | CTC | CGT | ACC | GAG | GTG | AAA | GTG | GCA | GAA | GAT | ATT | GCT | TCT | 1773 |
| Gln | Arg | Gly | Leu | Arg | Thr | Glu | Val | Lys | Val | Ala | Glu | Asp | Ile | Ala | Ser | |
| | | 35 | | | | | 40 | | | | | 45 | | | | |
| CCC | GTT | ACA | GCT | AAT | GCT | ATT | CAG | CAG | TTC | GTT | AAG | CAA | GAA | TAC | GAG | 1821 |
| Pro | Val | Thr | Ala | Asn | Ala | Ile | Gln | Gln | Phe | Val | Lys | Gln | Glu | Tyr | Glu | |
| | | 50 | | | | 55 | | | | | 60 | | | | | |
| AAA | GAA | GGT | AAT | GAT | TTG | ACC | TAT | GTT | CTT | TTG | GTT | GGC | GAT | CAC | AAA | 1869 |
| Lys | Glu | Gly | Asn | Asp | Leu | Thr | Tyr | Val | Leu | Leu | Val | Gly | Asp | His | Lys | |
| 65 | | | | | 70 | | | | | 75 | | | | | 80 | |
| GAT | ATT | CCT | GCC | AAA | ATT | ACT | CCG | GGG | ATC | AAA | TCC | GAC | CAG | GTA | TAT | 1917 |
| Asp | Ile | Pro | Ala | Lys | Ile | Thr | Pro | Gly | Ile | Lys | Ser | Asp | Gln | Val | Tyr | |
| | | | | 85 | | | | | 90 | | | | | 95 | | |
| GGA | CAA | ATA | GTA | GGT | AAT | GAC | CAC | TAC | AAC | GAA | GTC | TTC | ATC | GGT | CGT | 1965 |
| Gly | Gln | Ile | Val | Gly | Asn | Asp | His | Tyr | Asn | Glu | Val | Phe | Ile | Gly | Arg | |
| | | | 100 | | | | | 105 | | | | | 110 | | | |
| TTC | TCA | TGT | GAG | AGC | AAA | GAG | GAT | CTG | AAG | ACA | CAA | ATC | GAT | CGG | ACT | 2013 |
| Phe | Ser | Cys | Glu | Ser | Lys | Glu | Asp | Leu | Lys | Thr | Gln | Ile | Asp | Arg | Thr | |
| | | 115 | | | | | 120 | | | | | 125 | | | | |
| ATT | CAC | TAT | GAG | CGC | AAT | ATA | ACC | ACG | GAA | GAC | AAA | TGG | CTC | GGT | CAG | 2061 |
| Ile | His | Tyr | Glu | Arg | Asn | Ile | Thr | Thr | Glu | Asp | Lys | Trp | Leu | Gly | Gln | |
| | | 130 | | | | | 135 | | | | | 140 | | | | |
| GCT | CTT | TGT | ATT | GCT | TCG | GCT | GAA | GGA | GGC | CCA | TCC | GCA | GAC | AAT | GGT | 2109 |
| Ala | Leu | Cys | Ile | Ala | Ser | Ala | Glu | Gly | Gly | Pro | Ser | Ala | Asp | Asn | Gly | |
| 145 | | | | | 150 | | | | | 155 | | | | | 160 | |
| GAA | AGT | GAT | ATC | CAG | CAT | GAG | AAT | GTA | ATC | GCC | AAT | CTG | CTT | ACC | CAG | 2157 |
| Glu | Ser | Asp | Ile | Gln | His | Glu | Asn | Val | Ile | Ala | Asn | Leu | Leu | Thr | Gln | |
| | | | | 165 | | | | | 170 | | | | | 175 | | |
| TAT | GGC | TAT | ACC | AAG | ATT | ATC | AAA | TGT | TAT | GAT | CCG | GGA | GTA | ACT | CCT | 2205 |
| Tyr | Gly | Tyr | Thr | Lys | Ile | Ile | Lys | Cys | Tyr | Asp | Pro | Gly | Val | Thr | Pro | |
| | | | 180 | | | | | 185 | | | | | 190 | | | |
| AAA | AAC | ATT | ATT | GAT | GCT | TTC | AAC | GGA | GGA | ATC | TCG | TTG | GTC | AAC | TAT | 2253 |
| Lys | Asn | Ile | Ile | Asp | Ala | Phe | Asn | Gly | Gly | Ile | Ser | Leu | Val | Asn | Tyr | |
| | | 195 | | | | | 200 | | | | | 205 | | | | |
| ACG | GGC | CAC | GGT | AGC | GAA | ACA | GCT | TGG | GGT | ACG | TCT | CAC | TTC | GGC | ACC | 2301 |
| Thr | Gly | His | Gly | Ser | Glu | Thr | Ala | Trp | Gly | Thr | Ser | His | Phe | Gly | Thr | |
| | | 210 | | | | | 215 | | | | | 220 | | | | |
| ACT | CAT | GTG | AAG | CAG | CTT | ACC | AAC | AGC | AAC | CAG | CTA | CCG | TTT | ATT | TTC | 2349 |
| Thr | His | Val | Lys | Gln | Leu | Thr | Asn | Ser | Asn | Gln | Leu | Pro | Phe | Ile | Phe | |
| 225 | | | | | 230 | | | | | 235 | | | | | 240 | |
| GAC | GTA | GCT | TGT | GTG | AAT | GGC | GAT | TTC | CTA | TTC | AGC | ATG | CCT | TGC | TTC | 2397 |
| Asp | Val | Ala | Cys | Val | Asn | Gly | Asp | Phe | Leu | Phe | Ser | Met | Pro | Cys | Phe | |
| | | | | 245 | | | | | 250 | | | | | 255 | | |
| GCA | GAA | GCC | CTG | ATG | CGT | GCA | CAA | AAA | GAT | GGT | AAG | CCG | ACA | GGT | ACT | 2445 |
| Ala | Glu | Ala | Leu | Met | Arg | Ala | Gln | Lys | Asp | Gly | Lys | Pro | Thr | Gly | Thr | |
| | | | 260 | | | | | 265 | | | | | 270 | | | |
| GTT | GCT | ATC | ATA | GCG | TCT | ACG | ATC | AAC | CAG | TCT | TGG | GCT | TCT | CCT | ATG | 2493 |
| Val | Ala | Ile | Ile | Ala | Ser | Thr | Ile | Asn | Gln | Ser | Trp | Ala | Ser | Pro | Met | |
| | | | 275 | | | | | 280 | | | | | 285 | | | |
| CGC | GGG | CAG | GAT | GAG | ATG | AAC | GAA | ATT | CTG | TGC | GAA | AAA | CAC | CCG | AAC | 2541 |
| Arg | Gly | Gln | Asp | Glu | Met | Asn | Glu | Ile | Leu | Cys | Glu | Lys | His | Pro | Asn | |
| | | 290 | | | | | 295 | | | | | 300 | | | | |
| AAC | ATC | AAG | CGT | ACT | TTC | GGT | GGT | GTC | ACC | ATG | AAC | GGT | ATG | TTT | GCT | 2589 |
| Asn | Ile | Lys | Arg | Thr | Phe | Gly | Gly | Val | Thr | Met | Asn | Gly | Met | Phe | Ala | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| ATG | GTG | GAA | AAG | TAT | AAA | AAG | GAT | GGT | GAG | AAG | ATG | CTC | GAC | ACA | TGG | 2637 |
| Met | Val | Glu | Lys | Tyr | Lys | Lys | Asp | Gly | Glu | Lys | Met | Leu | Asp | Thr | Trp | |
| | | | 325 | | | | | 330 | | | | | 335 | | | |
| ACT | GTT | TTC | GGC | GAC | CCC | TCG | CTG | CTC | GTT | CGT | ACA | CTT | GTC | CCG | ACC | 2685 |
| Thr | Val | Phe | Gly | Asp | Pro | Ser | Leu | Leu | Val | Arg | Thr | Leu | Val | Pro | Thr | |
| | | | 340 | | | | 345 | | | | | 350 | | | | |
| AAA | ATG | CAG | GTT | ACG | GCT | CCG | GCT | CAG | ATT | AAT | TTG | ACG | GAT | GCT | TCA | 2733 |
| Lys | Met | Gln | Val | Thr | Ala | Pro | Ala | Gln | Ile | Asn | Leu | Thr | Asp | Ala | Ser | |
| | | 355 | | | | | 360 | | | | | 365 | | | | |
| GTC | AAC | GTA | TCT | TGC | GAT | TAT | AAT | GGT | GCT | ATT | GCT | ACC | ATT | TCA | GCC | 2781 |
| Val | Asn | Val | Ser | Cys | Asp | Tyr | Asn | Gly | Ala | Ile | Ala | Thr | Ile | Ser | Ala | |
| | 370 | | | | | 375 | | | | | 380 | | | | | |
| AAT | GGA | AAG | ATG | TTC | GGT | TCT | GCA | GTT | GTC | GAA | AAT | GGA | ACA | GCT | ACA | 2829 |
| Asn | Gly | Lys | Met | Phe | Gly | Ser | Ala | Val | Val | Glu | Asn | Gly | Thr | Ala | Thr | |
| 385 | | | | | 390 | | | | | 395 | | | | | 400 | |
| ATC | AAT | CTG | ACA | GGT | CTG | ACA | AAT | GAA | AGC | ACG | CTT | ACC | CTT | ACA | GTA | 2877 |
| Ile | Asn | Leu | Thr | Gly | Leu | Thr | Asn | Glu | Ser | Thr | Leu | Thr | Leu | Thr | Val | |
| | | | | 405 | | | | | 410 | | | | | 415 | | |
| GTT | GGT | TAC | AAC | AAA | GAG | ACG | GTT | ATT | AAG | ACC | ATC | AAC | ACT | AAT | GGT | 2925 |
| Val | Gly | Tyr | Asn | Lys | Glu | Thr | Val | Ile | Lys | Thr | Ile | Asn | Thr | Asn | Gly | |
| | | | 420 | | | | | 425 | | | | | 430 | | | |
| GAG | CCT | AAC | CCC | TAC | CAG | CCC | GTT | TCC | AAC | TTG | ACA | GCT | ACA | ACG | CAG | 2973 |
| Glu | Pro | Asn | Pro | Tyr | Gln | Pro | Val | Ser | Asn | Leu | Thr | Ala | Thr | Thr | Gln | |
| | | 435 | | | | | 440 | | | | | 445 | | | | |
| GGT | CAG | AAA | GTA | ACG | CTC | AAG | TGG | GAT | GCA | CCG | AGC | ACG | AAA | ACC | AAT | 3021 |
| Gly | Gln | Lys | Val | Thr | Leu | Lys | Trp | Asp | Ala | Pro | Ser | Thr | Lys | Thr | Asn | |
| | | 450 | | | | 455 | | | | | 460 | | | | | |
| GCA | ACC | ACT | AAT | ACC | GCT | CGC | AGC | GTG | GAT | GGC | ATA | CGA | GAA | TTG | GTT | 3069 |
| Ala | Thr | Thr | Asn | Thr | Ala | Arg | Ser | Val | Asp | Gly | Ile | Arg | Glu | Leu | Val | |
| 465 | | | | | 470 | | | | | 475 | | | | | 480 | |
| CTT | CTG | TCA | GTC | AGC | GAT | GCC | CCC | GAA | CTT | CTT | CGC | AGC | GGT | CAG | GCC | 3117 |
| Leu | Leu | Ser | Val | Ser | Asp | Ala | Pro | Glu | Leu | Leu | Arg | Ser | Gly | Gln | Ala | |
| | | | | 485 | | | | | 490 | | | | | 495 | | |
| GAG | ATT | GTT | CTT | GAA | GCT | CAC | GAT | GTT | TGG | AAT | GAT | GGA | TCC | | | 3159 |
| Glu | Ile | Val | Leu | Glu | Ala | His | Asp | Val | Trp | Asn | Asp | Gly | Ser | | | |
| | | | 500 | | | | 505 | | | | | 510 | | | | |

(2) INFORMATION FOR SEQ ID NO:5:

(i) SEQUENCE CHARACTERISTICS:
        (A) LENGTH: 737 amino acids
        (B) TYPE: amino acid
        (D) TOPOLOGY: linear (ii) MOLECULE TYPE: protein (xi) SEQUENCE DESCRIPTION: SEQ ID NO:5:

| | | | | | | | | | | | | | |
|---|---|---|---|---|---|---|---|---|---|---|---|---|---|
| Met | Lys | Asn | Leu | Asn | Lys | Phe | Val | Ser | Ile | Ala | Leu | Cys | Ser | Ser | Leu |
| -227 | | -225 | | | | -220 | | | | -215 | | | |

| Leu | Gly | Gly | Met | Ala | Phe | Ala | Gln | Gln | Thr | Glu | Leu | Gly | Arg | Asn | Pro |
|---|---|---|---|---|---|---|---|---|---|---|---|---|---|---|---|
| | -210 | | | | -205 | | | | | -200 | | | | | |

| Asn | Val | Arg | Leu | Leu | Glu | Ser | Thr | Gln | Gln | Ser | Val | Thr | Lys | Val | Gln |
|---|---|---|---|---|---|---|---|---|---|---|---|---|---|---|---|
| -195 | | | | | -190 | | | | | -185 | | | | | -180 |

| Phe | Arg | Met | Asp | Asn | Leu | Lys | Phe | Thr | Glu | Val | Gln | Thr | Pro | Lys | Gly |
|---|---|---|---|---|---|---|---|---|---|---|---|---|---|---|---|
| | | | | -175 | | | | | -170 | | | | | -165 | |

| Ile | Gly | Gln | Val | Pro | Thr | Tyr | Thr | Glu | Gly | Val | Asn | Leu | Ser | Glu | Lys |
|---|---|---|---|---|---|---|---|---|---|---|---|---|---|---|---|
| | | | | -160 | | | | | -155 | | | | | -150 | |

| Gly | Met | Pro | Thr | Leu | Pro | Ile | Leu | Ser | Arg | Ser | Leu | Ala | Val | Ser | Asp |
|---|---|---|---|---|---|---|---|---|---|---|---|---|---|---|---|
| | | | -145 | | | | | -140 | | | | | -135 | | |

| Thr | Arg | Glu | Met | Lys | Val | Glu | Val | Val | Ser | Ser | Lys | Phe | Ile | Glu | Lys |
|---|---|---|---|---|---|---|---|---|---|---|---|---|---|---|---|
| | | -130 | | | | | -125 | | | | | -120 | | | |

-continued

```
Lys Asn Val Leu Ile Ala Pro Ser Lys Gly Met Ile Met Arg Asn Glu
-115               -110               -105                    -100

Asp Pro Lys Lys Ile Pro Tyr Val Tyr Gly Lys Ser Tyr Ser Gln Asn
            -95               -90                    -85

Lys Phe Phe Pro Gly Glu Ile Ala Thr Leu Asp Asp Pro Phe Ile Leu
        -80               -75               -70

Arg Asp Val Arg Gly Gln Val Val Asn Phe Ala Pro Leu Gln Tyr Asn
        -65               -60                    -55

Pro Val Thr Lys Thr Leu Arg Ile Tyr Thr Glu Ile Thr Val Ala Val
        -50               -45               -40

Ser Glu Thr Ser Glu Gln Gly Lys Asn Ile Leu Asn Lys Lys Gly Thr
-35                 -30               -25                    -20

Phe Ala Gly Phe Glu Asp Thr Tyr Lys Arg Met Phe Met Asn Tyr Glu
            -15               -10                         -5

Pro Gly Arg Tyr Thr Pro Val Glu Glu Lys Gln Asn Gly Arg Met Ile
                1             5                      10

Val Ile Val Ala Lys Lys Tyr Glu Gly Asp Ile Lys Asp Phe Val Asp
        15              20                  25

Trp Lys Asn Gln Arg Gly Leu Arg Thr Glu Val Lys Val Ala Glu Asp
30              35                  40                      45

Ile Ala Ser Pro Val Thr Ala Asn Ala Ile Gln Gln Phe Val Lys Gln
                50                  55                      60

Glu Tyr Glu Lys Glu Gly Asn Asp Leu Thr Tyr Val Leu Leu Val Gly
        65                  70                  75

Asp His Lys Asp Ile Pro Ala Lys Ile Thr Pro Gly Ile Lys Ser Asp
        80                  85                  90

Gln Val Tyr Gly Gln Ile Val Gly Asn Asp His Tyr Asn Glu Val Phe
        95              100                 105

Ile Gly Arg Phe Ser Cys Glu Ser Lys Glu Asp Leu Lys Thr Gln Ile
110             115                 120                     125

Asp Arg Thr Ile His Tyr Glu Arg Asn Ile Thr Thr Glu Asp Lys Trp
                130                 135                     140

Leu Gly Gln Ala Leu Cys Ile Ala Ser Ala Glu Gly Gly Pro Ser Ala
            145                 150                 155

Asp Asn Gly Glu Ser Asp Ile Gln His Glu Asn Val Ile Ala Asn Leu
        160                 165                 170

Leu Thr Gln Tyr Gly Tyr Thr Lys Ile Ile Lys Cys Tyr Asp Pro Gly
    175                 180                 185

Val Thr Pro Lys Asn Ile Ile Asp Ala Phe Asn Gly Gly Ile Ser Leu
190                 195                 200                 205

Val Asn Tyr Thr Gly His Gly Ser Glu Thr Ala Trp Gly Thr Ser His
                210                 215                     220

Phe Gly Thr Thr His Val Lys Gln Leu Thr Asn Ser Asn Gln Leu Pro
            225                 230                 235

Phe Ile Phe Asp Val Ala Cys Val Asn Gly Asp Phe Leu Phe Ser Met
        240                 245                 250

Pro Cys Phe Ala Glu Ala Leu Met Arg Ala Gln Lys Asp Gly Lys Pro
    255                 260                 265

Thr Gly Thr Val Ala Ile Ile Ala Ser Thr Ile Asn Gln Ser Trp Ala
270                 275                 280                 285

Ser Pro Met Arg Gly Gln Asp Glu Met Asn Glu Ile Leu Cys Glu Lys
                290                 295                 300

His Pro Asn Asn Ile Lys Arg Thr Phe Gly Gly Val Thr Met Asn Gly
```

|     |     |     |     |     | 305 |     |     |     |     | 310 |     |     |     |     | 315 |
|-----|-----|-----|-----|-----|-----|-----|-----|-----|-----|-----|-----|-----|-----|-----|-----|

Met Phe Ala Met Val Glu Lys Tyr Lys Lys Asp Gly Glu Lys Met Leu
        320                 325                 330

Asp Thr Trp Thr Val Phe Gly Asp Pro Ser Leu Leu Val Arg Thr Leu
    335                 340                 345

Val Pro Thr Lys Met Gln Val Thr Ala Pro Ala Gln Ile Asn Leu Thr
350                 355                 360                     365

Asp Ala Ser Val Asn Val Ser Cys Asp Tyr Asn Gly Ala Ile Ala Thr
                370                 375                     380

Ile Ser Ala Asn Gly Lys Met Phe Gly Ser Ala Val Val Glu Asn Gly
                385                 390                 395

Thr Ala Thr Ile Asn Leu Thr Gly Leu Thr Asn Glu Ser Thr Leu Thr
        400                 405                 410

Leu Thr Val Val Gly Tyr Asn Lys Glu Thr Val Ile Lys Thr Ile Asn
    415                 420                 425

Thr Asn Gly Glu Pro Asn Pro Tyr Gln Pro Val Ser Asn Leu Thr Ala
430                 435                 440                     445

Thr Thr Gln Gly Gln Lys Val Thr Leu Lys Trp Asp Ala Pro Ser Thr
                450                 455                 460

Lys Thr Asn Ala Thr Thr Asn Thr Ala Arg Ser Val Asp Gly Ile Arg
                465                 470                 475

Glu Leu Val Leu Leu Ser Val Ser Asp Ala Pro Glu Leu Leu Arg Ser
        480                 485                 490

Gly Gln Ala Glu Ile Val Leu Glu Ala His Asp Val Trp Asn Asp Gly
    495                 500                 505

Ser
510

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:6:

Glu Leu Leu Arg
1

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( i i i ) HYPOTHETICAL: NO ( x i ) SEQUENCE DESCRIPTION: SEQ ID NO:7:

GGCTTTACNC CNGTNGARGA RYTNGA 26

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( i i i ) HYPOTHETICAL: NO ( x i ) SEQUENCE DESCRIPTION: SEQ ID NO:8:

GGCTTTRTTY TTCCARTCNA CRAARTCYTT 30

( 2 ) INFORMATION FOR SEQ ID NO:9:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( i i i ) HYPOTHETICAL: NO ( x i ) SEQUENCE DESCRIPTION: SEQ ID NO:9:

CCTGGAGAAT TCTCGTATGA TCGTCATCGT AGCCAAAAAG TATGAGGG 48

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (other nucleic acid)

( i i i ) HYPOTHETICAL: NO ( x i ) SEQUENCE DESCRIPTION: SEQ ID NO:10:

ATCAACACTA ATGGTGAGCC 20

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:11:

Ser Cys Asp Tyr Asn Gly Ala Ile Ala Thr Ile Ser Ala
1               5                   10

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:12:

Ser Cys Trp Ala Phe Ser Gly Val Ala Ala Thr Phe Ser Ala
1               5                   10

( 2 ) INFORMATION FOR SEQ ID NO:13:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:13:

Ser Cys Trp Ile Phe Ser Thr Ile Gly Ala Leu Phe Ser Ala
1               5                   10

( 2 ) INFORMATION FOR SEQ ID NO:14:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:14:

Gly Cys Trp Ala Phe Ser Ala Ile Ala Thr Val Glu Gly Ile
1               5                   10

( 2 ) INFORMATION FOR SEQ ID NO:15:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:15:

Ser Cys Trp Ala Phe Ser Ala Val Val Thr Ile Phe Gly Ile
1               5                   10

( 2 ) INFORMATION FOR SEQ ID NO:16:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:16:

```
Ser  Cys  Trp  Ala  Phe  Gly  Ala  Val  Glu  Ala  Ile  Ser  Asp  Arg
1                   5                        10
```